(12) United States Patent
McCulloch et al.

(10) Patent No.: US 11,766,267 B2
(45) Date of Patent: Sep. 26, 2023

(54) ARTICULATING SURGICAL TOOL

(71) Applicant: Invictus Orthopaedics LLC, Teaneck, NJ (US)

(72) Inventors: Kenneth McCulloch, Manhasset, NY (US); Anthony D'Antuono, South Amboy, NJ (US); Troy Lane, Murrells Inlet, SC (US)

(73) Assignee: Invictus Orthopaedics LLC, Teaneck, NJ (US)

( * ) Notice: Subject to any disclaimer, the term of this patent is extended or adjusted under 35 U.S.C. 154(b) by 627 days.

(21) Appl. No.: 16/691,271

(22) Filed: Nov. 21, 2019

(65) Prior Publication Data

US 2020/0085448 A1 Mar. 19, 2020
US 2023/0190310 A9 Jun. 22, 2023

Related U.S. Application Data

(63) Continuation of application No. 15/627,723, filed on Jun. 20, 2017, now abandoned.
(Continued)

(51) Int. Cl.
*A61B 17/16* (2006.01)
*A61F 2/46* (2006.01)
(Continued)

(52) U.S. Cl.
CPC ........ *A61B 17/1668* (2013.01); *A61B 17/164* (2013.01); *A61F 2/4607* (2013.01);
(Continued)

(58) Field of Classification Search
CPC . A61B 17/1668; A61B 17/1659; A61B 17/92; A61B 17/921; A61B 2017/922;
(Continued)

(56) References Cited

U.S. PATENT DOCUMENTS 2,638,092 A 5/1953 Dorr
5,261,915 A 11/1993 Durlacher et al.
(Continued)

FOREIGN PATENT DOCUMENTS

CN 102665591 B 9/2012
CN 103750925 A 4/2014
(Continued)

OTHER PUBLICATIONS

Examination Report dated Jun. 26, 2021 in Indian Patent Application No. 201917000707 (6 sheets).
(Continued)

*Primary Examiner* — Amy R Sipp
(74) *Attorney, Agent, or Firm* — Collard & Roe, P.C.

(57) ABSTRACT

A surgical instrument for releasable connection to a surgical tool having two or more sections that are able to articulate 360 degrees in differing increments and directions. The articulation of the sections allows for the distal end to be spatially offset from the proximal, yet maintain parallel longitudinal axes. The surgical instrument includes a force disc at the proximal end upon which a surgeon can exert a linear force which is transmitted to the distal end having a second tool such as a broach firmly attached thereto.

13 Claims, 44 Drawing Sheets

Related U.S. Application Data

(60) Provisional application No. 62/510,111, filed on May 23, 2017, provisional application No. 62/353,261, filed on Jun. 22, 2016.

(51) Int. Cl.
　　*A61B 17/00* (2006.01)
　　*A61F 2/30* (2006.01)
　　*A61F 2/32* (2006.01)

(52) U.S. Cl.
　　CPC ... *A61B 17/1659* (2013.01); *A61B 2017/0046* (2013.01); *A61F 2/32* (2013.01); *A61F 2002/30471* (2013.01); *A61F 2002/30538* (2013.01)

(58) Field of Classification Search
　　CPC ..... A61B 2017/924; A61F 2002/30538; A61F 2002/30471; A61F 2/4607; A61F 2/4603
　　See application file for complete search history.

(56) References Cited

U.S. PATENT DOCUMENTS

| | | | |
|---|---|---|---|
| 5,665,091 A * | 9/1997 | Noble | A61B 17/1659 606/85 |
| 6,966,916 B2 | 11/2005 | Kumar | |
| 7,591,821 B2 | 9/2009 | Kelman | |
| 8,992,542 B2 | 3/2015 | Hagag et al. | |
| 9,554,810 B2 | 1/2017 | Tsukayama et al. | |
| 9,796,074 B2 | 10/2017 | Mugnier | |
| 10,327,827 B2 | 6/2019 | Young et al. | |
| 10,568,644 B2 | 2/2020 | Tsukayama et al. | |
| 2008/0109006 A1* | 5/2008 | Waltersdorff | A61B 17/92 16/110.1 |
| 2008/0255565 A1 | 10/2008 | Fletcher | |
| 2012/0059359 A1* | 3/2012 | Burgi | A61B 17/1659 606/1 |
| 2012/0083769 A1 | 4/2012 | Burgi et al. | |
| 2013/0325020 A1 | 12/2013 | Yoko et al. | |
| 2014/0163561 A1 | 6/2014 | Sharp et al. | |
| 2014/0207123 A1 | 7/2014 | Mueller | |

FOREIGN PATENT DOCUMENTS

| | | |
|---|---|---|
| CN | 104042309 A | 9/2014 |
| CN | 104873243 A | 9/2015 |
| CN | 105120805 A | 12/2015 |
| DE | 20 2012 102 894 U1 | 8/2012 |
| WO | 2015/198005 A1 | 12/2015 |

OTHER PUBLICATIONS

International Preliminary Report on Patentability dated Dec. 25, 2018 in International Application PCT/US2017/038263 (6 sheets).
Written Opinion of the International Searching Authority dated Sep. 29, 2017 in International Application PCT/US2017/038263 (6 sheets).
Supplementary European Search Report dated Jan. 23, 2020 in European Application No. 17816045.3-1122 (6 sheets).
International Search Report dated Sep. 29, 2017 in International Application PCT/US2017/038263 (2 sheets).
First Office Action dated Dec. 25, 2020 in Chinese Patent Application No. 201780051019.0 (7 sheets); English translation attached (4 sheets).
Second Office Action dated Aug. 20, 2021 in Chinese Patent Application No. 201780051019.0 (4 sheets); English translation attached (3 sheets).
Office Action dated May 22, 2019 in U.S. Appl. No. 15/627,723 (15 sheets).
Patent Certificate dated Jul. 15, 2022 in Indian Patent Application No. 201917000707 (1 sheet).
Communication letter ("Intimation of the grant and recordal of patent under section 43 of the Act in respect of patent application No. 201917000707") dated Jul. 15, 2022 in Indian Patent Application No. 201917000707 (1 sheet).

* cited by examiner

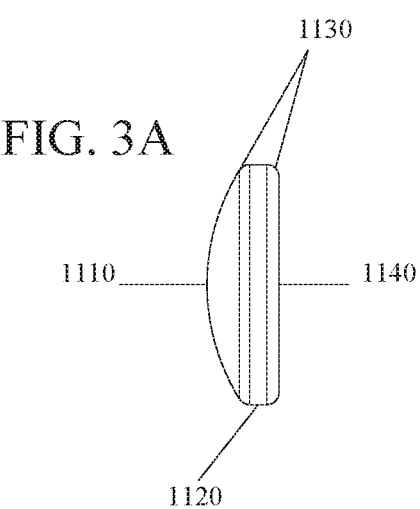
FIG. 3A
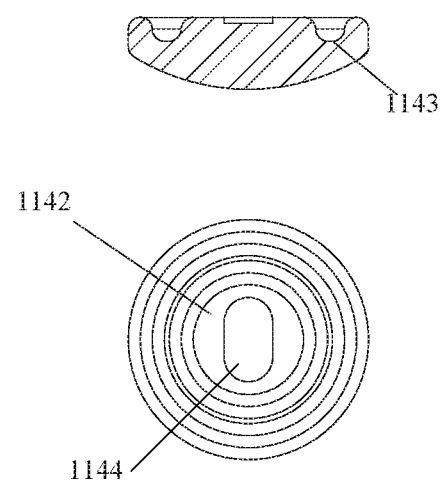
FIG. 3C
FIG. 3B

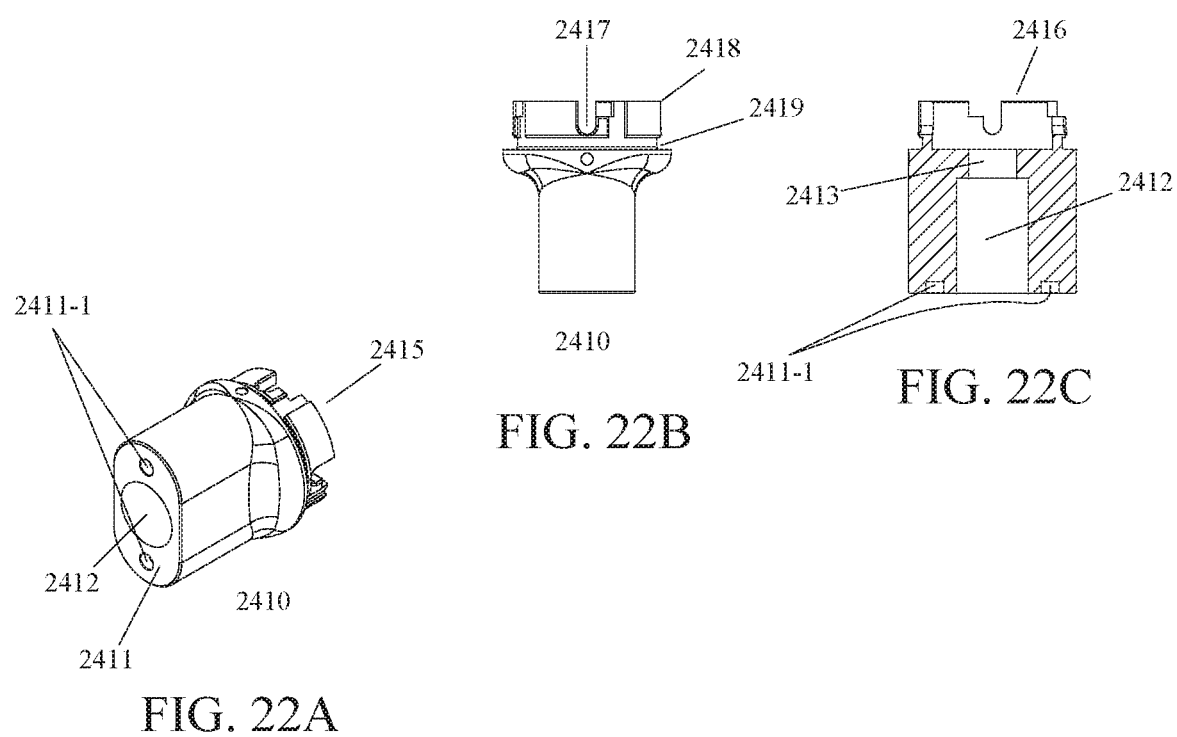

FIG. 23C
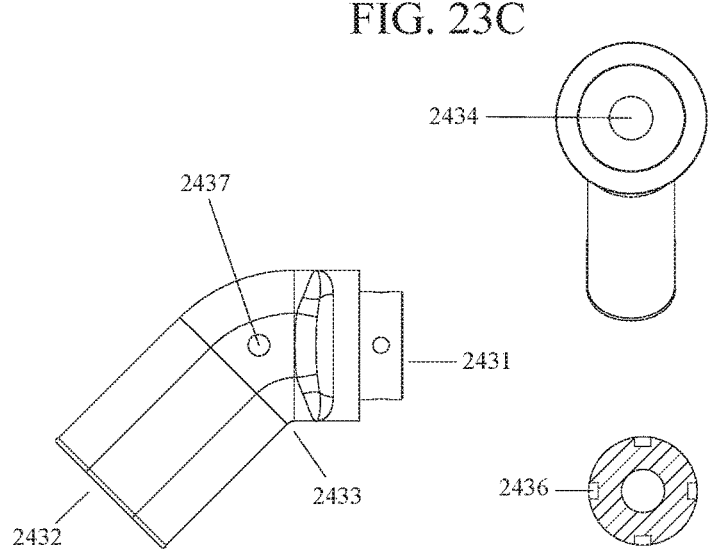
FIG. 23A
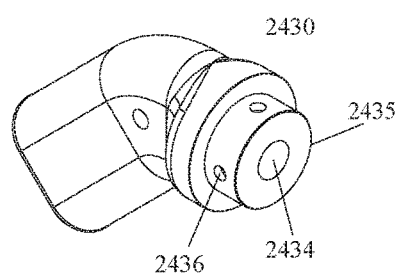
FIG. 23B  FIG. 23D

FIG. 29C
FIG. 29D
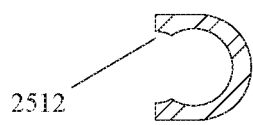
2512
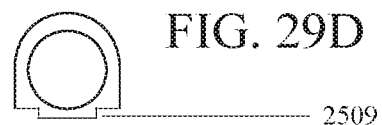
2509
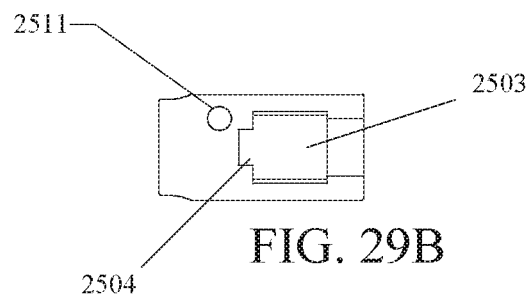
2511
2503
2504
FIG. 29B
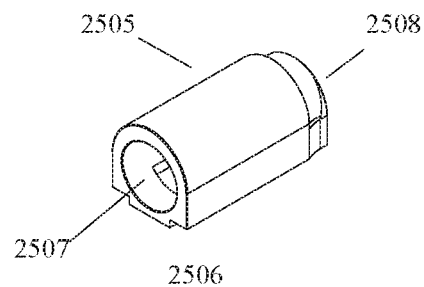
2505   2508
2507
2506
FIG. 29A

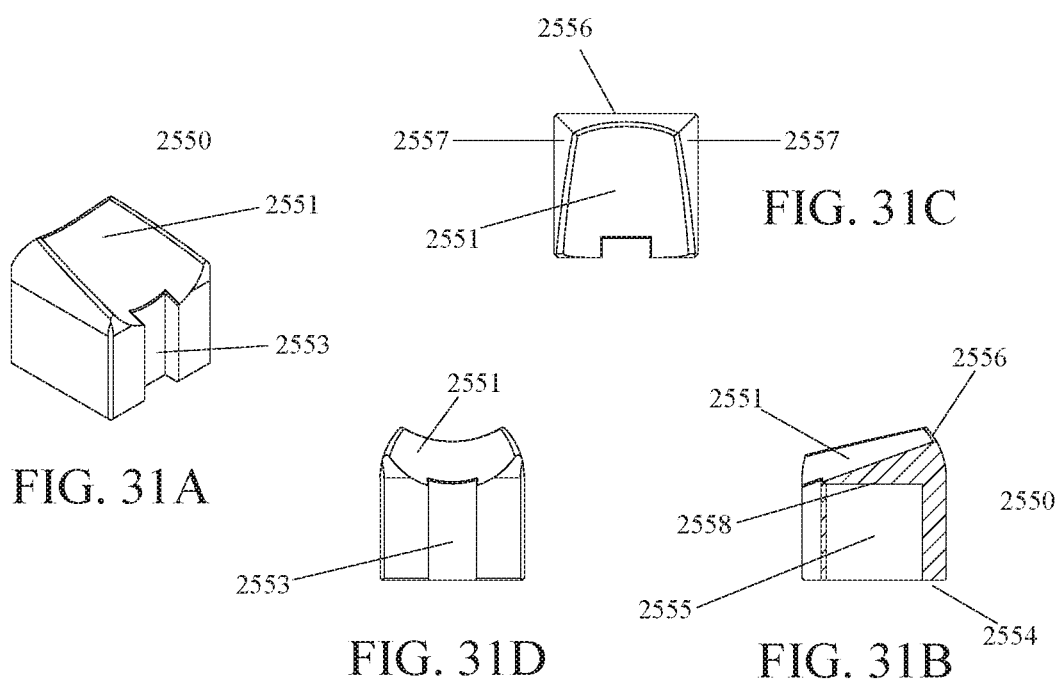

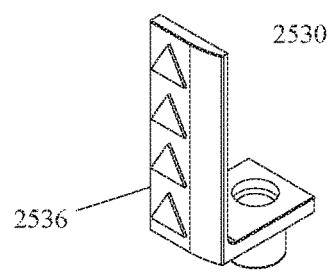
FIG. 33A
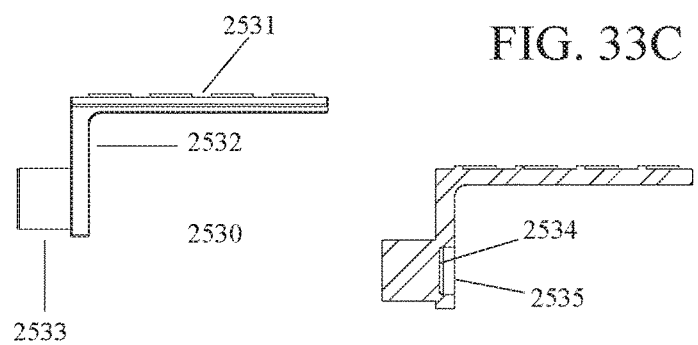
FIG. 33B
FIG. 33C

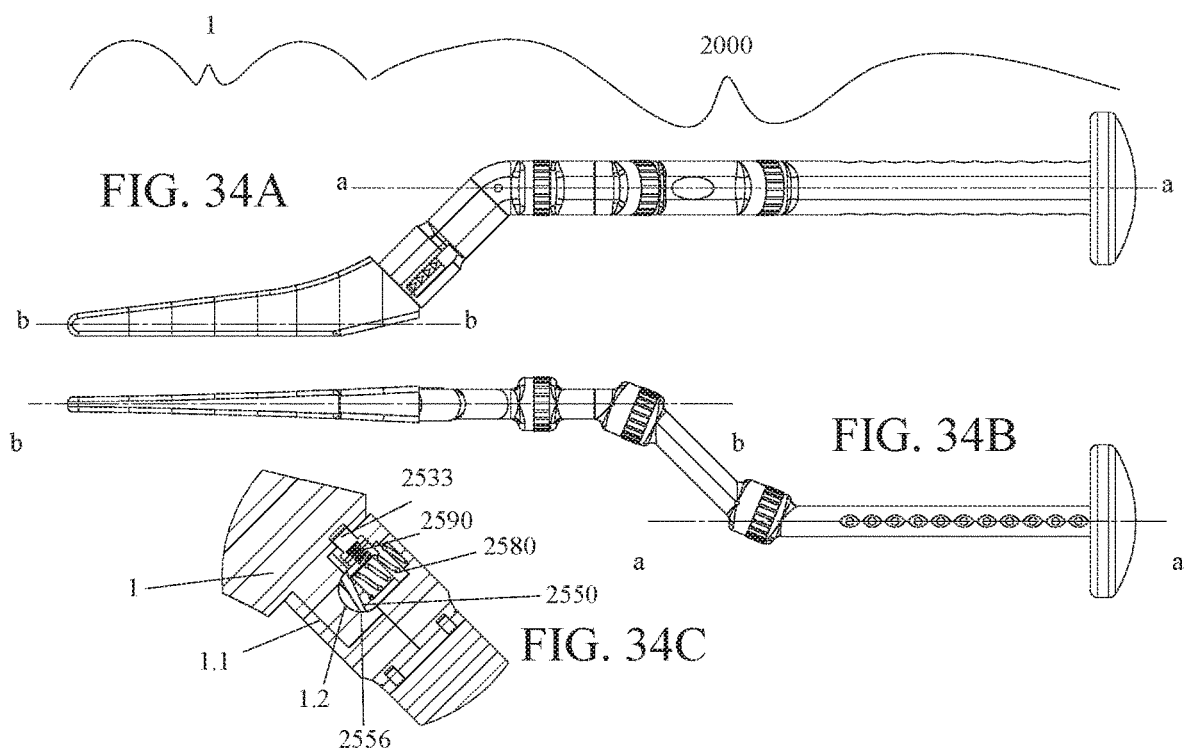

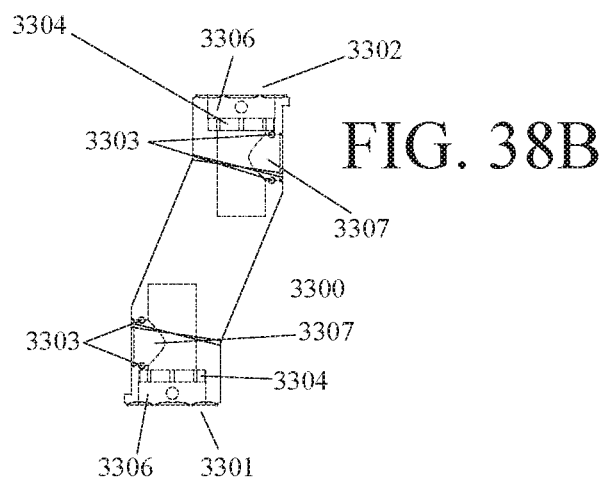
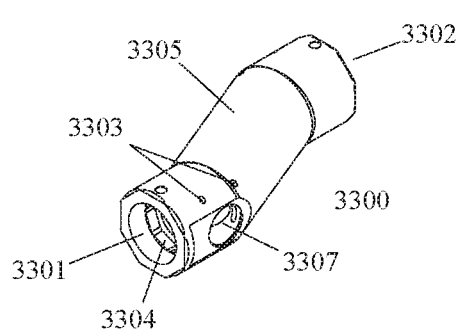
FIG. 38A
FIG. 38B

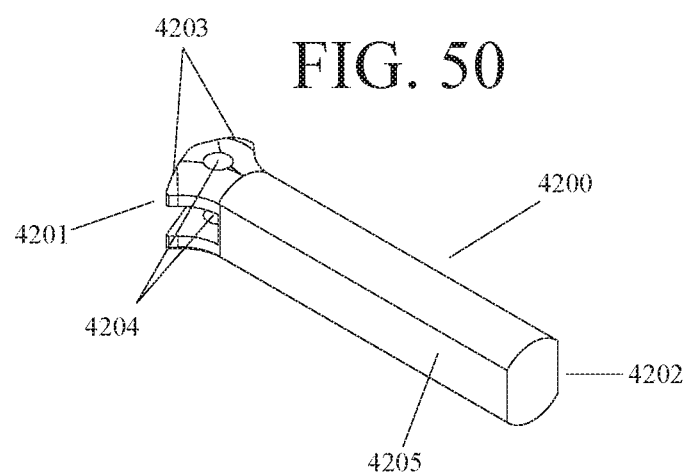

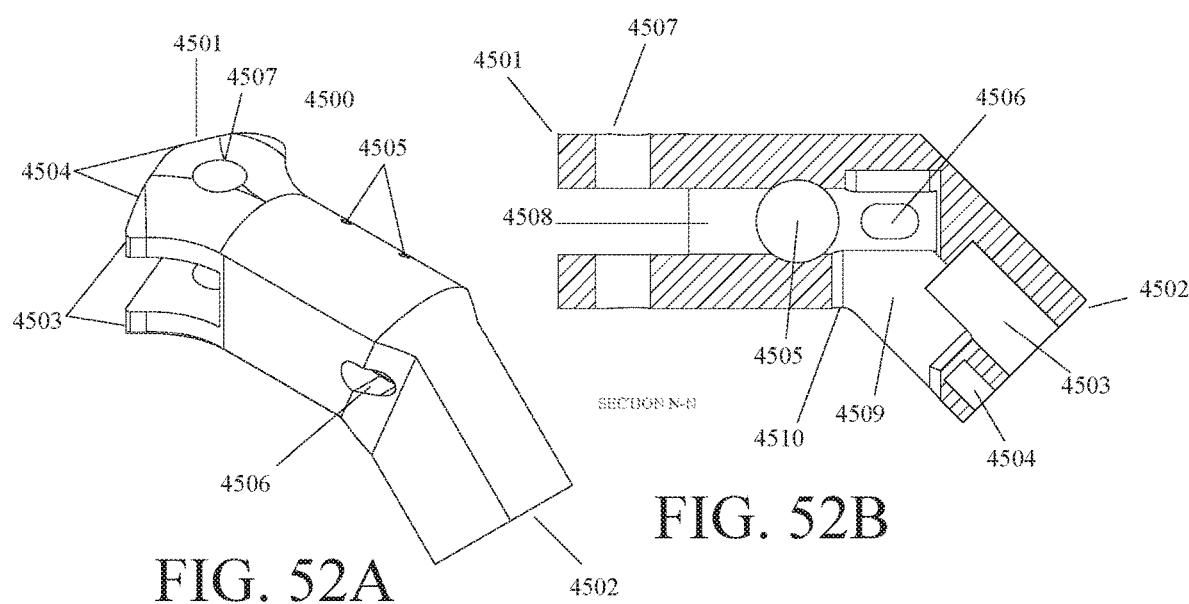

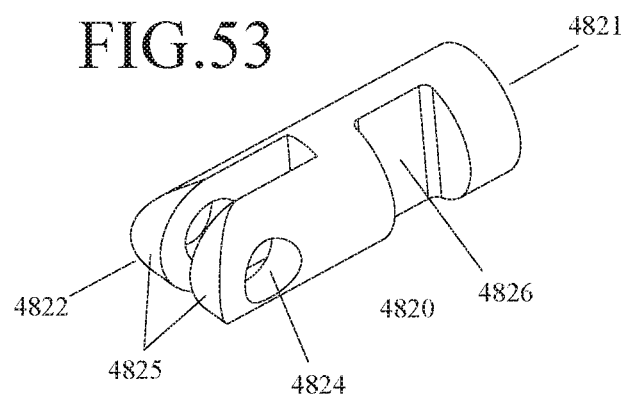

ARTICULATING SURGICAL TOOL

CROSS REFERENCE TO RELATED APPLICATIONS

The present application is a Continuation of U.S. patent application Ser. No. 15/627,723, filed on Jun. 20, 2017, which claims the benefit of U.S. Provisional Application No. 62/353,261, filed on Jun. 22, 2016, and U.S. Provisional Application No. 62/510,111, filed on May 23, 2017. The entire contents of each of the above being incorporated herein by reference.

FIELD OF THE INVENTION

The present invention generally relates to surgical instruments used in minimal incision surgery aiding in the installation of orthopedic prosthesis, and more particularly, to a surgical instrument having a releaseable connection to another surgical tool for preparing a bone site prior to the implantation of a hip prosthesis' femoral component during hip replacement surgery.

BACKGROUND OF THE INVENTION

Joint implants, also referred to as, for example, joint prostheses or joint replacements, are long-term surgically implantable devices that are used to partially or totally replace diseased or damaged joints, such as a hip, a knee, a shoulder, an ankle, or an elbow, within the musculoskeletal system of a human or an animal. Artificial hip joints are generally ball and socket joints, designed to match as closely as possible the function of the natural joint. Generally, the artificial socket is implanted in one bone, and the artificial ball articulates in the socket. A stem structure attached to the ball is implanted in another of the patient's bones, securing the ball in position.

The ball and socket joint of the human hip unites the femur to the pelvis. The head of the femur or ball fits into the acetabulum of the pelvis, forming a joint which allows the leg to move forward, backward, and sideways in a wide range.

Various degenerative diseases and injuries may necessitate replacement of all or a portion of a hip using synthetic materials. Prosthetic components are generally made from metals, ceramics, or plastics, or combinations of them.

Total hip arthroplasty and hemi-arthroplasty are two well-known procedures for replacing all or part of a patient's hip. A total hip arthroplasty replaces both the femoral component and the acetabular surface of the joint. A hemi-arthroplasty may replace either the femoral component or the acetabular surface of the joint. The purpose of hip replacement surgery is to remove the damaged and worn parts of the hip and replace them with artificial parts, called prostheses, with the purpose of at least partially restoring the hip's function, including but not limited to, restoring the stability, strength, range of motion, and flexibility of the joint.

In total hip replacement surgery, a patient's natural hip is replaced by two main components: an acetabular cup component that replaces the acetabular socket, and the femoral component, or the stem-and-ball component that replaces the femoral head.

In order to install the acetabular cup, a surgeon prepares the bone by reaming the acetabular socket to create a surface for accepting a cup. The cup may be held in place by bone cement or an interference or press fit, or it may have a porous outer surface suitable for bony ingrowth. The new acetabular shell is implanted securely within the prepared hemispherical socket.

Next, the femur is prepared to receive the stem. The proximal end of the femur is at least partially resected to expose the central portion of the bone. In the central portion, a cavity is created that matches the shape of the implant stem. The top end of the femur is planed and smoothed so that the stem can be inserted flush with the bone surface.

It is highly desirable to adapt the surgical instruments used in preparation of the femoral bone during hip replacement to minimally invasive surgery, computer assisted surgery, or both. The instruments used in femoral preparation include, but are not limited to, osteotomes or chisels used for resecting at least a portion of the femoral head to expose the central portion of the femur, and broaches, reamers, and rasps, used to clean and enlarge the hollow center of the bone, creating a cavity that matches the shape of the femoral component's stem.

During hip replacement surgery, the surgeon opens a femoral intramedullary canal by removing a portion of the trochanteric fossa with an osteotome or a chisel, an instrument for surgical division or sectioning of bone. The surgeon then uses one or a series of increasing size cavity preparation devices, such as reamers or broaches, to prepare a cavity for installation of a femoral stem. By using a series of gradually increasing in size devices, the surgeon expands the intrafemoral cavity until the desired size and shape is created. Sometimes, the portion of the final broach inserted into the femoral cavity serves as a trial femoral stem.

It is generally desired to select and install the femoral stem of the largest size suitable for a particular patient. Electing the largest appropriate femoral stem helps to stabilize the femoral component in the femur, improves alignment, and reduces the potential of the femoral component's loosening and failure. There is a need for instruments and method for preparation of a femoral cavity that permit installation of an appropriately sized stem of the femoral component in order to improve alignment and stabilization of the femoral component in the patient with minimum interference the tissue of the patient In minimally invasive surgery, the need to insert and operate the femoral preparation instruments through smaller incisions may conflict with the proper instrument alignment needed to create the cavity of the largest possible size. For proper access and alignment, long incisions and other invasive procedures are often required. The single-incision lateral or posterior approach hip-arthroplasty procedure may simplify access to the femur. A direct anterior approach for minimally invasive total hip arthroplasty has become increasingly popular. Preparation of the femoral canal using this approach can be technically challenging. Instrumentation of the femur involves a posteromedial capsular release, extension and external rotation of the operative leg and elevation of the femur anteriorly. Curved offset femoral broaches have been specifically designed to safely prepare the femoral canal through this single incision. A broach handle with lateral and anterior offset for the direct anterior approach has been developed to reduce the need for leverage of the proximal femur for preparation of the cavity.

Because a surgeon may perform a left hip replacement surgery or a right hip replacement surgery, it is currently necessary that the surgeon have both left and right lateral offset broach handles. Similarly, depending on a patient's body type, i.e., large protruding mid-section, current offset broach handles may not have adequate offset to account for such patients. Thus, it is necessary to have a broach handle that is adaptable to different situations and conditions.

In summary, there is a current unrealized need for improved devices, systems and procedures adapted for use in minimally invasive surgery (MIS). There is a particular unrealized need for improved devices for preparation of a patient's femur for installing a femoral component of a hip prosthesis. Improved devices are desired that are adapted for introduction and operation through a smaller surgical incision than conventionally available devices. Also needed are improved devices, systems, and procedures that would minimize the damage to the flesh, muscle, and other soft tissues during insertion, operation, and withdrawal. At the same time, there is a need for improved devices, systems, and procedures that would improve sizing and aligning of the femoral components and reduce the risk of their loosening. In general, devices and systems are needed that are easy to use and manufacture, minimize tissue damage, simplify surgical procedures, are versatile, allow for faster healing with fewer complications, require less post-surgical immobilization, and are less costly to produce and operate.

SUMMARY OF THE INVENTION

The foregoing and other problems and deficiencies in known broach handles are solved and a technical advantage is achieved by an articulating broach handle.

An object of the present invention is an articulating surgical tool handle, comprising a force disc, two or more longitudinal sections, one or more articulating means, and means for releasably attaching a tool. Wherein the one or more articulating means allow each of the two or more sections to rotate 360 degrees with respect to the other sections.

A further object of the present invention is that the one or more articulating means allows articulation of the two or more sections in discrete increments.

Another object of the present invention is that the two or more longitudinal sections may comprise one or more of the following, a Main Section, a Center Section, a Connecting Body and a Broach Section, and the two articulating means allow for a double offset configuration.

Still a further object of the present invention is that in the double offset configuration, the Main Section is offset spatially from the Broach Section and maintain parallel axes of the longitudinal Main and Broach Sections.

Another further object of the present invention is that the spatial offset of the Main and Broach Sections is adjustable by the two articulating means.

Yet another object of the present invention is that the discrete increments are of the range of 22.5 degrees to 45 degrees of rotation.

Another object of the present invention is that the articulating means comprises a cam mechanism, wherein the cam mechanism allows for the adjustment of the position of the two or more sections relative to each other, and the cam mechanism allows for the two or more sections to be in a fixed position relative to the other of the two or more sections.

Another object of the present invention is a method of using an articulating surgical tool handle to prepare a patient's femur for installing a prosthetic stem component into the medullary canal of the femur. The method comprises the steps of providing an articulating surgical tool handle to attach a broach for installing a prosthetic stem component. The articulating surgical tool handle comprises a force disc, a main longitudinal section, a center longitudinal section, a connecting body longitudinal section, a broach section, a first articulating means connecting the main longitudinal section and the center longitudinal section, a second articulating means connecting the center longitudinal section and the connecting body section, and a broach section connected to the connecting body longitudinal section. The method further includes the steps of attaching a broach to the broach section, adjusting the first and second articulating means to spatially offset the main longitudinal section from the broach section, inserting the articulating surgical tool handle and broach into the medullary canal through a surgical incision, positioning the articulating surgical tool handle and broach, preparing the medullary canal by striking the force disc to create a femoral canal, and removing the articulating surgical tool handle and broach from the medullary canal. The articulating surgical tool handle can be configured for either a left or right hip replacement surgery, and depending on the physical characteristics of a patient, the spatial offset between the main longitudinal section and the broach section can be adjusted using one or both of the articulating means.

Other devices, apparatuses, methods, features, and advantages of this invention will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWINGS

The foregoing summary, as well as the following detailed description of the invention will be better understood when read in conjunction with the appended drawings. It should be understood, however, that the invention can be embodied in different forms and thus should not be construed as being limited to the embodiments set forth herein.

FIG. 3A is perspective view of the Force Disc;

FIG. 3B is a view of the backside of the Force Disc;

FIG. 3C is a cross section view of the Force Disc;

FIG. 22A is a perspective view of a 180 Pull of the embodiment depicted in FIG. 12;

FIG. 22B is a front view of the 180 Pull of the embodiment depicted in FIG. 12;

FIG. 22C is a cross-sectional view of the 180 Pull of the embodiment depicted in FIG. 12;

FIG. 23A is a perspective view of a 180 Junction of the embodiment depicted in FIG. 12;

FIG. 23B is a side view of the 180 Junction of the embodiment depicted in FIG. 12;

FIG. 23C is a front view of the 180 Junction of the embodiment depicted in FIG. 12;

FIG. 23D is a cross-sectional view of a 180 Junction Slip Fit Journal of the embodiment depicted in FIG. 12;

FIG. 29A is a perspective view of the top half of a Broach Section of the embodiment depicted in FIG. 12;

FIG. 29B is a cross-sectional top view of the top half of the Broach Section of the embodiment depicted in FIG. 12;

FIG. 29C is a cross-sectional front view of the top half of the Broach Section of the embodiment depicted in FIG. 12;

FIG. 29D is a front view of the top half of the Broach Section of the embodiment depicted in FIG. 12;

FIG. 31A is a perspective view of a Pillow Block of the embodiment depicted in FIG. 13A;

FIG. 31B is a cross-sectional side view of the Pillow Block of the embodiment depicted in FIG. 13A;

FIG. 31C is a top view of the Pillow Block of the embodiment depicted in FIG. 13A;

FIG. 31D is a front view of the Pillow Block of the embodiment depicted in FIG. 13A;

FIG. 33A is a perspective view of a Slide Release of the embodiment depicted in FIG. 12;

FIG. 33B is a side view of the Slide Release of the embodiment depicted in FIG. 12;

FIG. 33C is a cross-sectional side view of the Slide Release of the embodiment depicted in FIG. 12;

FIG. 34A is a side view of the embodiment depicted in FIG. 12 with a Broach attached to the distal end;

FIG. 34B is top view of the embodiment depicted in FIG. 12 with a Broach attached to the distal end;

FIG. 34C is a cross-sectional view of the engaging mechanism of the Broach Section of the embodiment depicted in FIG. 12 with the Broach;

FIG. 38A is a top view of the Center Section of the embodiment of the articulating broach handle of FIG. 35;

FIG. 38B is a cut-away view of the Center Section of FIG. 38A;

FIG. 50 is a perspective view of the Main Section of the embodiment of the articulating broach handle of FIG. 49A;

FIG. 52A is a perspective view of the Broach Section of the embodiment of the articulating broach handle of FIG. 49A;

FIG. 52B is a cut-away view of the Broach Section of FIG. 52A; and

FIG. 53 is a perspective view of the Clasp Rod of the cut-away view of the Broach Section of FIG. 52B.

DETAILED DESCRIPTION

The present subject matter will now be described more fully hereinafter with reference to the accompanying figures, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

By way of a prophetic example, the following description of the present invention is directed to an articulating broach handle with a releasable connection to a broach that has two or more sections that each can articulate 360 degrees. The specification describes four (4) prophetic embodiments. Each embodiment composed of hardened 420 stainless steel, hardened 440 steel and/or titanium. It is also contemplated that the inner components are constructed from either hardened 420 or hardened 440 stainless steel and the external components are constructed of titanium. However, other forms of surgical steel may be used. One of ordinary skill in the art will understand that the description of the invention is not limited to a broach handle.

Embodiment 1

Figure 1:
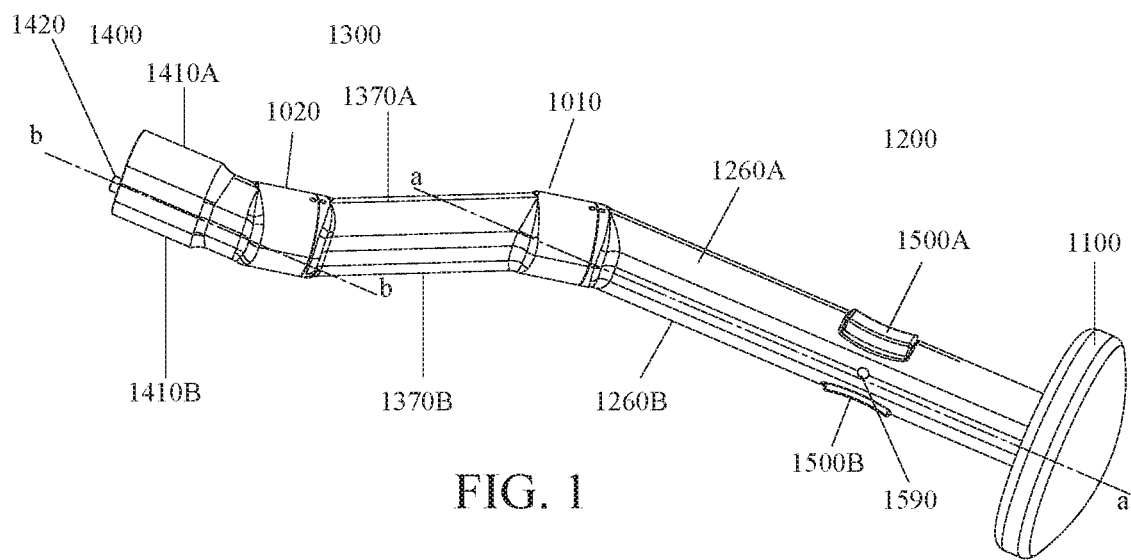
FIG. 1 is a perspective view of an embodiment of an articulating broach handle.

FIG. 1 depicts a first embodiment of the present invention as described in the context of a broach handle 1000. The broach handle from the proximal end to the distal end consists of a Force Disc 1100, a Main Section 1200, First and Second Triggers 1500A, 1500B, a Center Section 1300, and a Broach Section 1400. Each section (Main, Center and Broach) is constructed in two mirrored halves, top (a) and bottom (b) halves. The halves are semi-permanent or permanently affixed together. Semi-permanent attachment of the mirrored halves (sections) allow for disassembly. Each section is substantially solid with the exception of channels and cavities allowing the broach handle's internal components (described later) to be housed without excessive movement when assembled.

The proximal end of the Broach Handle 1000 comprises a circular shaped Force Disc 1100 (FIGS. 3A, 3B) and may have chamfered edges 1130. The diameter of the Force Disc is preferably 2.5 inches and a total thickness of 0.75 inches, comprising an arcing dome surface (convex surface) 1110 projecting approximately 0.3 inches from a uniform side 1120 having a thickness of approximately 0.4 inches. The arcing dome surface serves as an infinite vectoring force distribution. The proximal surface 1110 is convex with a radius of approximately 2.27 inches. The distal side 1140 of the Force Disc 1100 is contoured such that the outer edge 1141 and center portion 1142 of the Force Disc is thicker than the midway portion 1143 (FIGS. 3B and 3C). The midway portion 1143 of the distal side 1140 of the Force Disc forms a 360 degree channel. This allows for allocating the center of mass and enhancing the ergonomics by balancing the overall instrument assembly for better functionality. The center portion 1142 of the distal side 1140 of the Force Disc includes a first cavity 1144 allowing the proximal end 1270 of the Main Section 1200 to permanently or semi-permanently affix to the Force Disc 1100. The perimeter of the first cavity 1144 is shaped similar to the proximal end 1270 of the Main Section, allowing a force fit between the Force Disc and the Main Section. The proximal end 1270 of the Main Section 1200 once assembled with the Force Disc 1100 may be permanently or semi-permanently attached together by a weld or other known fixation methods.

The Main Section 1200 (FIG. 4) is a longitudinal linear shaft 1261 with a bend (1262) at the distal end 1280. The bend 1262 is preferably between 50 and 80 degrees, and more preferably 67.5 degrees. The length of the Main Section 1200 from the proximal end 1270 to the bend 1262 is approximately 5.145 inches. From the bend 1262 to the absolute distal end is approximately 0.5 inches. The width of the Main Section 1200 is approximately 0.5 inches and has a height of approximately 0.4375 inches along the longitudinal linear shaft 1261. The distal end 1280 of the Main Section 1200 at the bend 1262 and beyond in the distal direction is cylindrical. The diameter of the bend is 0.875 inches and the absolute distal end has a diameter of 0.6250 inches. The above measurements and those following are exemplary figures. Other dimensions are contemplated.

Figure 4:
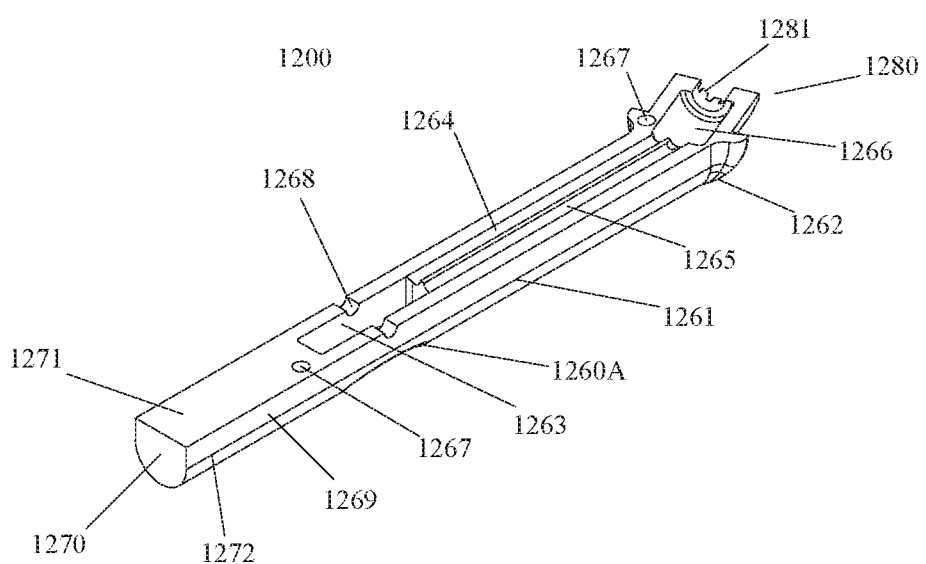
FIG. 4 is a perspective view of one half of the Main Section.

The Main Section 1200 comprises two mirrored halves/sections 1260A, 1260B along the longitudinal length. For clarity, only the bottom mirrored section is depicted in FIG. 4. For convenience, the Applicant has omitted the suffix 'B' from the reference designators for the individual parts of the bottom mirrored section 1260B. Where appropriate and necessary, Applicant has included the suffixes 'A' and 'B'.

Each mirrored section, includes a trigger well 1263, two channels 1264, 1265 extending along the longitudinal shaft, a second cavity 1266 to house the proximal end 1231 of a first connector 1230 and a first spring 1240, two cylindrical blind holes 1267 and a third channel 1268 centered on the trigger well 1263 and transverse to the longitudinal shaft 1261. The profile of the Main Section longitudinal shaft 1261 has two parallel sides 1269 connected by a circular external side 1272 and a relatively flat inner side 1271, where the inner side 1271 of the two mirrored sections 1260A, 1260B are mated together when the two mirrored sections are assembled. The mirrored sections may be permanently (welded) or semi-permanently attached to each other along the inner sides.

Figures 2A, 2B:
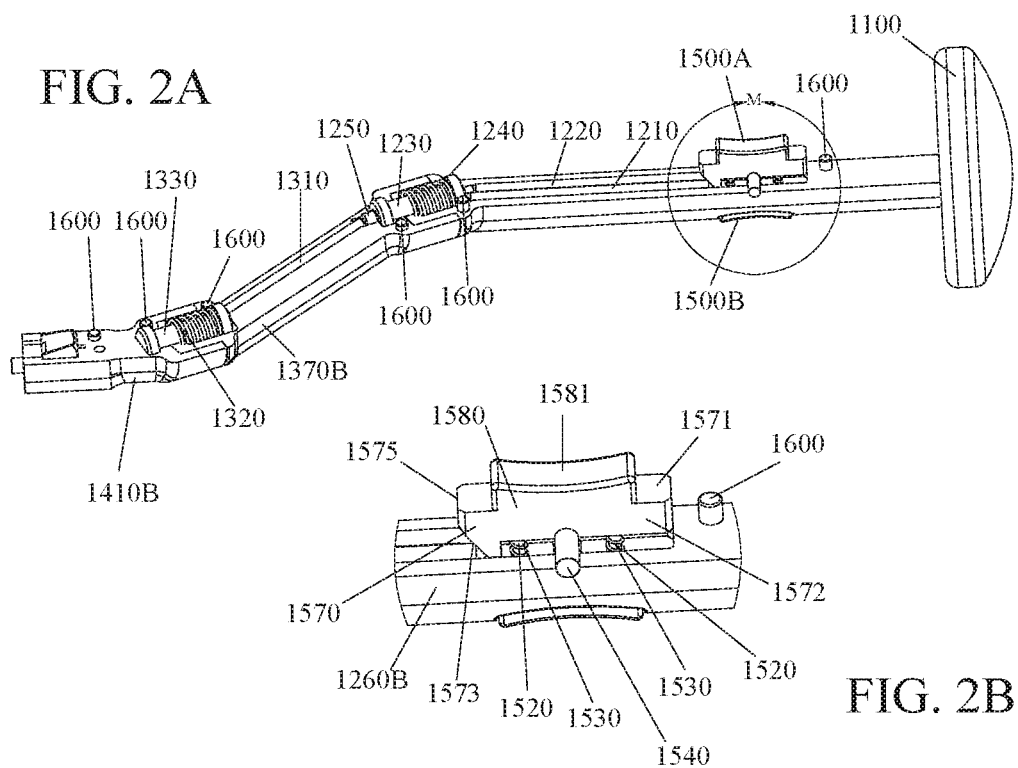
FIG. 2A is a cut-away view of and embodiment of the articulating broach handle exposing the interior components.
FIG. 2B is a exploded view of the trigger mechanism of the embodiment of the articulating broach handle.

Identical dowels 1600 (FIGS. 2A and 2B) are inserted into the two cylindrical blind holes 1267 to align the two mirrored sections 1260A, 1260B when assembled.

The trigger well 1263 of each mirrored section 1260A, 1260B extends through the width of each mirrored section such that the opening on the external side 1272 is smaller than the opening on the internal side (flat inner side) 1271. This allows the First and Second Triggers 1500A, 1500B to be seated within the Main Section 1200 and are secured once the two mirrored sections are assembled.

The two channels 1264, 1265 of the longitudinal shaft extend from the distal end of the trigger well 1263 to the proximal end of the second cavity 1266. Each channel has a concave profile with a depth of preferably 0.0525 inches. The two channels 1264, 1265 are sized to fit one each of two transfer rods 1210, 1220

The distal end 1280 of each mirrored section 1260A, 1260B is semi-cylindrical with trapezoid-shaped gear teeth 1281 having a depth of approximately 0.0595 inches extending therefrom.

Figure 10:
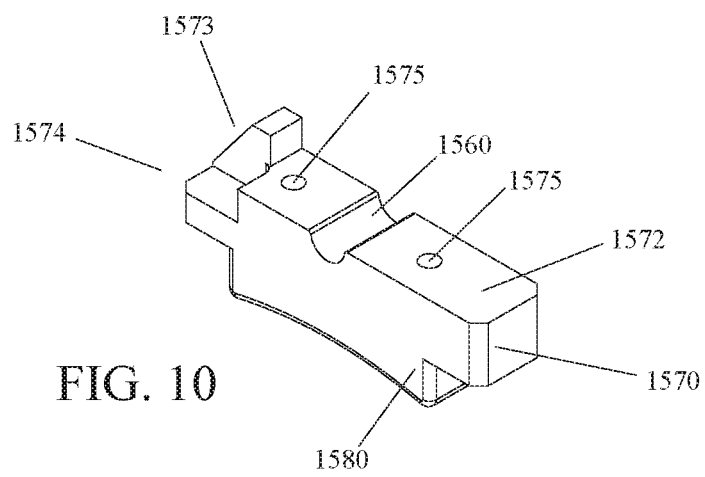
FIG. 10 is a perspective view of the Trigger mechanism.

The First and Second Triggers (FIG. 10) include a main body 1570 and a raised member 1580 with a concave surface 1581. The raised member 1580, extends beyond the main body upper surface and has a length of 0.750 inches. The concave surface 1581 is designed to ergonomically be compatible with the human thumb. The main body 1570 has a length of 1.1125 inches. The trigger has a width of approximately 0.250 inches. The distal end 1574 of the trigger includes a vertical side 1575 extending downward from the top surface 1571 of the main body and a slanted surface 1573 extending further downward beyond the bottom surface 1572 of the main body 1570. The slanted surface 1573 is positioned on one side of the width of the trigger (the left side when facing the distal end 1574 of the trigger). Transverse to the length of the trigger is a trigger channel 1560 extending the width of the trigger in the bottom surface 1572 of the trigger 1500. The trigger channel 1560 is coincident with the third channel 1268 of the Main Section 1200.

Spaced equal distances on either side of the trigger channel 1560 are two cylindrical holes 1575 on the bottom surface 1572 of the trigger 1500. Each hole 1575 has an initial diameter and a subsequent smaller diameter. The larger diameter component of the hole is to house a trigger spring 1520 while the small diameter houses the trigger pin 1530 which may be pressed fit into the cylindrical hole 1575 and surrounded by the trigger spring 1520.

The trigger channel and the third channel 1268 of the Main Section 1200 when assembled allow for the insertion of a Trigger Center Pin 1540 which allows keeping the First and Second Triggers 1500A, 1500B aligned.

The slanted surface 1573 of Trigger 1500A (top trigger) is cooperatively in contact with transfer rod 1210 which rests in the left channel 1264 (FIG. 4) when viewing the Main Section 1200 from proximal to distal end. The slanted surface 1573 of Trigger 1500B (bottom trigger) is cooperatively in contact with transfer rod 1220 which rests in the right channel 1265 when viewing the Main Section 1200 from proximal 1270 to distal end 1280.

Figure 7A:
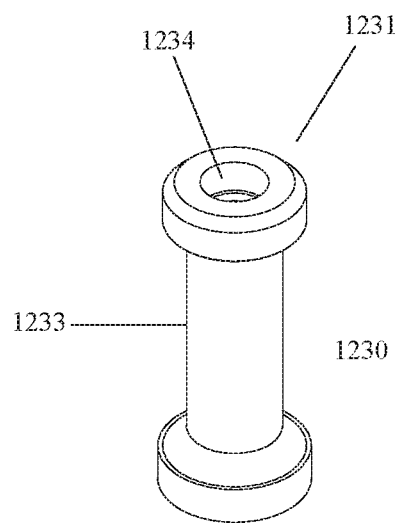
FIG. 7A is a perspective view of the First Connector.
Figure 7B:
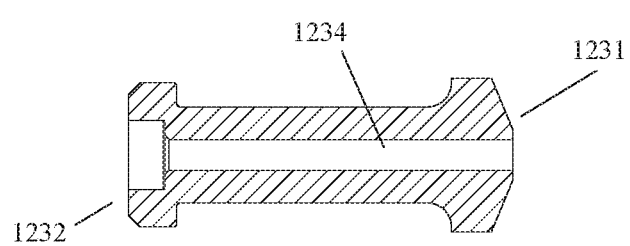
FIG. 7B is a cross-section of the First Connector.

The first connector 1230 (FIGS. 7A, 7B) which connects the Main Section 1200 and the Center Section 1300 is cylindrical and bar bell-shape. Both the proximal end 1231 and the distal end 1232 of the first connector 1230 have a greater diameter than the mid-section 1233. The proximal end 1231 is generally a convex surface while the distal end 1232 is flat, perpendicular to the longitudinal length of the first connector 1230. The first connector has a cylindrical channel 1234 running the length of the first connector. The diameter of the cylindrical channel, 0.0800 inches, is consistent throughout the length of the first connector except at the distal end 1232. At the distal end 1232, the diameter of the cylindrical channel is 0.1800 inches.

Figure 9:
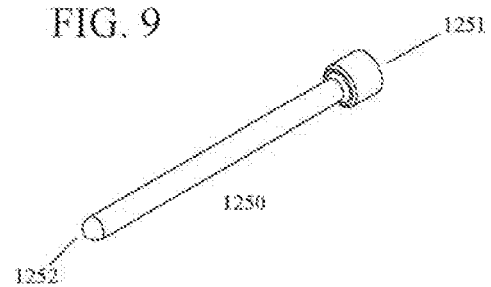
FIG. 9 is a perspective view of the Engagement Pin.

The cylindrical channel 1234 is sized to allow an engagement pin 1250 (FIG. 9) to be inserted and movable. The engagement pin 1250 has a length of 1.265 inches and a diameter of 0.08 inches. The distal end 1251 of the engagement pin 1250 has greater diameter such that the distal end 1252 of the engagement pin fits can be seated within the enlarged diameter of the cylindrical channel 1234 at the distal end 1232 of the first connector 1230, when no forces are acting on the Broach Handle 1000.

Encircling the proximal end 1231 of the first connector 1230 within the mid-section 1233 is a first spring 1240 which is housed in the second cavity 1266 at the distal end 1280 of the Main Section 1200.

Figure 11:
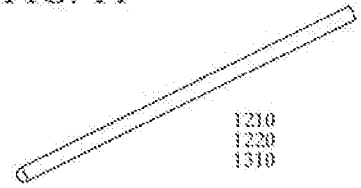
FIG. 11 is a perspective view of the Transfer Rod(s).
Figure 12:
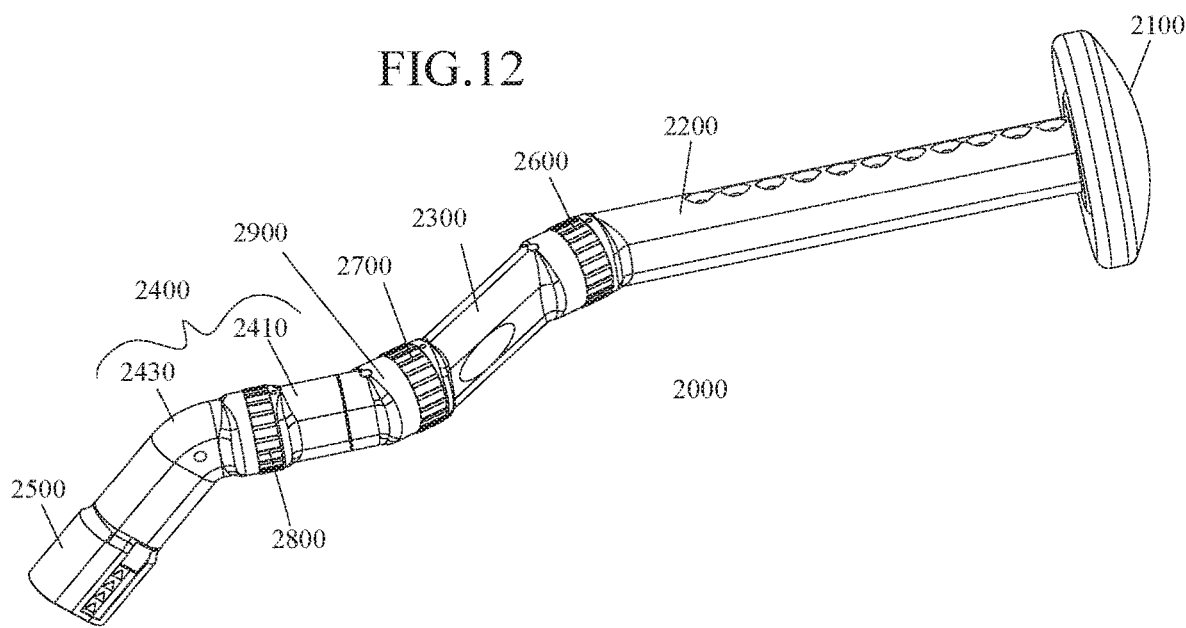
FIG. 12 is a perspective view of a embodiment of the present invention.
Figure 13:
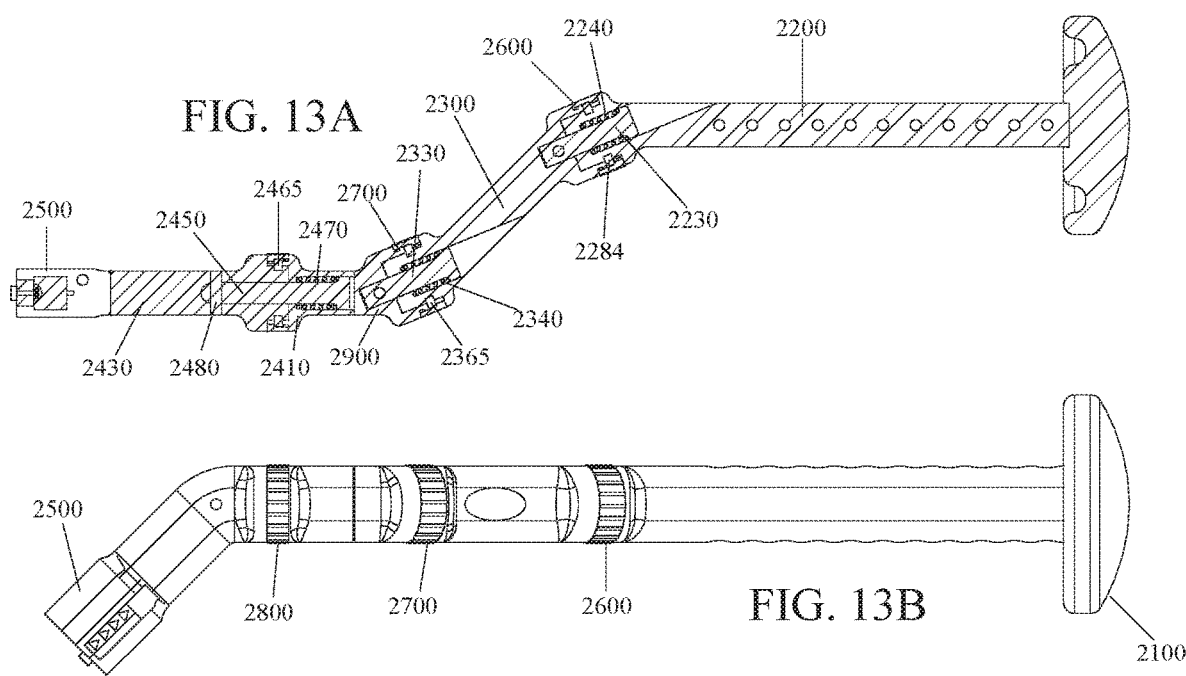
FIG. 13A is a cut away view of the embodiment depicted in FIG. 12.
FIG. 13B is a side view of the embodiment depicted in FIG. 12.

Transfer rods 1210, 1220 (FIG. 11) have a length of 2.580 inches and a radius of 0.05 inches. Transfer rod 1220 is cooperatively in contact with engagement pin 1250 and the slanted surface 1573 of bottom trigger 1500B, such that when bottom trigger 1500B is actuated, the slanted surface 1573 causes transfer rod 1220 to move distally causing the engagement pin 1250 to move distally as well.

Transfer rod 1210 is cooperatively in contact with the proximal end 1231 of the first connector 1230 and the slanted surface 1573 of top trigger 1500A, such that when top trigger 1500A is actuated, the slanted surface 1573 causes transfer rod 1210 to move distally further causing the first connector 1230 to move distally.

Figure 5A:
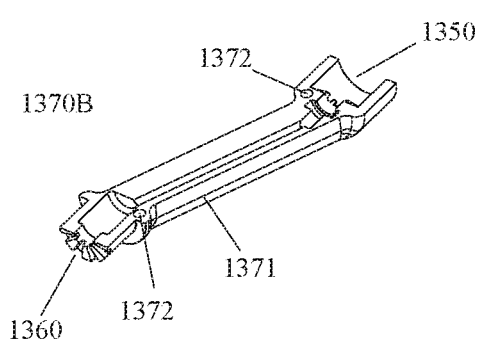
FIG. 5A is a perspective view of one half of the Center Section.
Figure 5B:
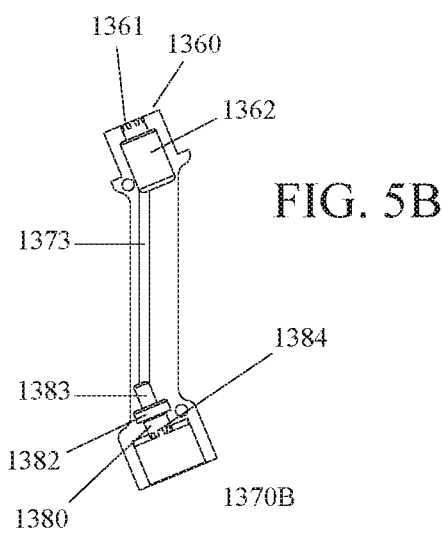
FIG. 5B is cross section view of the Center Section.

The Center Section 1300 (FIGS. 5A and 5B) of the Broach Handle 1000 interconnects the Main Section 1200 and the Broach Section 1400. The Center Section 1300 comprises a proximal end 1350 which is angled at 67.5 degrees from the center shaft 1371 and a distal end 1360 which is angled at 67.5 degrees in the opposite direction.

Similar to the Main Section 1200, the Center Section 1300 (FIGS. 5A and 5B) comprises two mirrored sections 1370A (shown in FIG. 1), 1370B along the longitudinal length. Applicant's designation of individual elements of the mirrored sections of the Center Section is the same as that for the Main Section 1200, and will also be the same for the Broach Section 1400. The proximal end 1350 is approximately 0.775 inches in length, the center shaft 1371 is approximately 2.3512 inches in length, and the distal end is approximately 0.497 inches length for a total length (taking into consideration the offset angles of both the proximal and distal ends) of 3.6752 inches. The Center Section 1300 includes two cylindrical blind holes 1372 and a fourth channel 1373 extending the length of the center shaft 1371.

The proximal end 1350 of the Center Section 1300 comprises an open three tiered cavity 1380 which is shaped to house the distal end 1280 of the Main Section 1200 (first tier cavity 1381), the distal end 1232 of the first connector 1230 (second tier cavity 1382) and an extended length of 0.250 inches allowing the distal end 1251 of the engagement pin 1250 to move distally when acted upon (third tier cavity 1383).

The distal end of the first tier cavity 1381 includes trapezoid-shaped gear teeth 1384 having a depth of approximately 0.0595 inches which are compatible to the equivalent teeth 1281 of the distal end 1280 of the Main Section 1200.

The second tier cavity 1382 is shaped according to the distal end 1232 of the first connector 1230 such that the first connector 1230 when assembled into the second tier cavity 1382 is firmly secured in the second tier cavity. The third tier cavity 1383 is cylindrically shaped allowing the engagement pin 1250 to move distally when acted upon by the 1220 transverse rod. The distal end of the third tier cavity 1383 cooperatively mates with the fourth channel 1373 which extends the length of the center shaft 1371.

The distal end 1360 of the Center Section 1300 is configured identical to that of the distal end 1280 of the Main Section 1200. That is, the distal end 1360 of each mirrored section 1370A, 1370B includes a third cavity 1362 to house the proximal end 1331 of the second connector 1330 and spring 1320 and is semi-circular with trapezoid-shaped gear teeth 1361 having a depth of approximately 0.0595 inches.

Figure 6B:
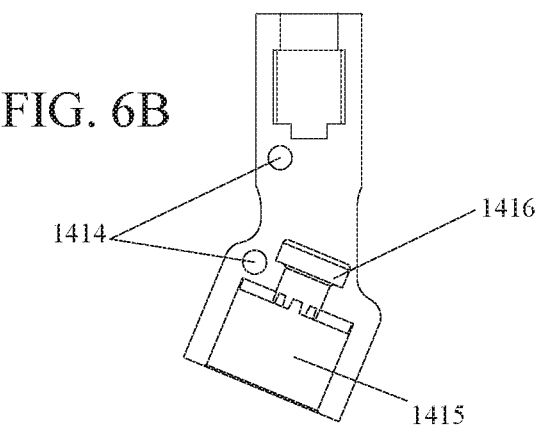
FIG. 6B is a cross section view of the Broach Section.
Figure 6A:
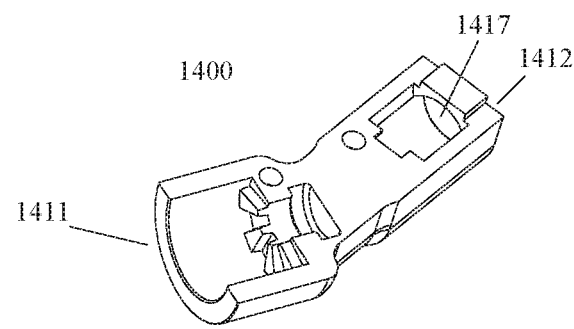
FIG. 6A is a perspective view of one half of the Broach Section.

The Broach Section 1400 (FIGS. 6A, 6B) allows for a Broach (not shown) to the Broach Handle. The proximal end 1411 of the Broach Section is similar in structure as that of the proximal end of the Center Section having a main cavity 1415 whose distal end includes trapezoid-shaped gear teeth. A second cavity 1416 shaped according to the distal end of second connector 1330. The distal end 1412 of the Broach Section includes a cavity 1417 for housing the proximal end of a Broach. Two cylindrical blind-holes 1414 allow dowels 1600 to be inserted such that when the two mirrored sections of the Broach Section are assembled the dowels allow alignment between the mirrored sections.

Figure 8:
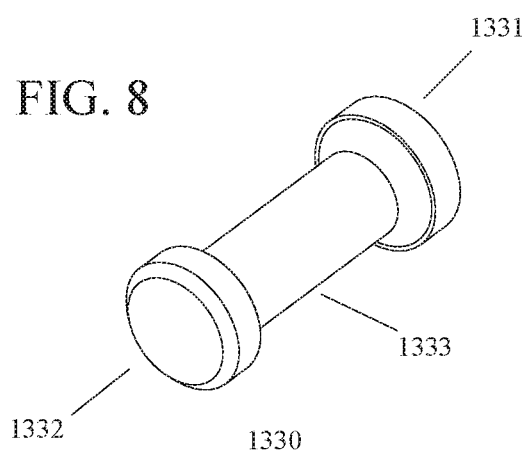
FIG. 8 is a perspective view of the Second Connector.

The second connector 1330 (FIG. 8) which connects the Center Section 1300 and the Broach Section 1400 is cylindrical and bar bell-shaped. Both the proximal end 1331 and the distal end 1332 of the second connector 1330 have a greater diameter than the mid-section 1333. The proximal end 1331 has a generally convex surface while the distal end 1332 is flat with a beveled edge, perpendicular to the longitudinal length of the second connector 1330. Unlike the first connector 1230, the second connector 1330 is solid and does not have a cylindrical shaft running the length of the connector.

When assembled, the proximal end 1331 of the second connector 1330 fits within the third cavity 1362 of the distal end 1360 of the Center Section 1300 and is encircled by spring 1320, identical configuration to that of the first connector assembly.

A third transfer rod 1310 fits within the fourth channel 1373 of the center shaft 1371 of the Center Section 1300. The third transfer rod is cooperatively in contact with the distal end 1251 of the engagement pin 1250 and the proximal end 1331 of the second connector 1330.

Two identical dowels 1600 are inserted into the two cylindrical blind-holes 1372 such that when the two mirrored sections 1370A, 1370B of the Center Section are assembled the dowels allow alignment between the mirrored sections. The Broach Section 1400 of the Broach Handle interconnects on the distal end a Broach with the Broach Section. The Broach Section comprises a proximal end which is angled at 67.5 degrees from the center shaft. The center shaft of the Broach handle is approximately 0.4 inches in length and the distal end is approximately 0.650 inches in length. The distal end of the Broach Section is approximately 0.75 inches in length. The Broach Section may have two cylindrical blind holes. The distal end of the Broach Section may include a Broach Lock Pin 1420 preventing the Broach from rotating about the b axis.

The proximal end of both the top and bottom section of the Broach Section 1400 are mirrored sections, similar in construction as the proximal end of the Center Section with the exception of the three tiered cavity of the Center Section. The proximal end of the top and bottom sections of the Broach Section has a two-tiered cavity, where the first tiered cavity (proximal cavity) is identical to the first tier cavity of the Center Section that allows for housing the distal end of the Center Section. The second tier cavity (distal cavity) is shaped to according to the distal end of the second connector, such that the second connector when assembled into the second tier cavity is firmly secured in the second tier cavity.

The distal end of the top section of the Broach Section comprises a cylindrical hole with a diameter of 0.806 inches extending approximately 0.575 inches towards the proximal end. A slot on the flat surface of the Broach Section extends the length of the cylindrical hole. The top section of the Broach Section has a channel transverse to the longitudinal length of the Broach Section. This channel is sized to fit a Broach Dowel.

The distal end of the bottom section of the Broach Section comprises a cylindrical hole extending toward the proximal end. Similar to the top section of the Broach Section, the bottom section has a channel traversing the longitudinal length of the Broach Section.

Alternatively, the distal end of the Broach Section may comprise the engaging mechanism of the Broach Section from Embodiment 2 and/or 3 of the present invention (described later).

When the two mirrored sections 1370A, 1370B of the Center Section 1300 are assembled with the two mirrored sections 1260A, 1260B of the Main Section 1200 such that the distal end 1280 of the Main Section 1200 is seated in the first tier cavity 1381 of the Center Section, 15 cooperating gear teeth 1281, 1361 are formed allowing the Main Section and the Center Section to articulate in 24 degree increments. The number of cooperating gear teeth 1281, 1361 determines the amount of articulation of the Main and Center sections. In the example provided, 15 cooperating gear teeth are formed. Increasing the number of cooperating gear teeth results in a smaller articulation increment, while fewer cooperating gear teeth increases the amount of incremental articulation. For example, 30 cooperating gear teeth results in 12 degrees of articulation per increment. Whereas, 8 cooperating gear teeth results in 45 degrees of articulation per increment.

When the two mirrored sections 1410A, 1410B of the Broach Section 1400 are assembled with the two mirrored sections 1370A, 1370B of the Center Section 1300 such that the distal end 1360 of the Center Section 1300 is seated in a cavity of the Broach Section 1400, 15 cooperating gear teeth are formed allowing the Center Section and the Broach Section to articulate in 24 degree increments, independent of the articulating means of the Main Section 1200 and Center Section 1300. The articulating means function in the same manner as that between the Main Section and the Center Section.

A unique feature of the present invention as described in the above embodiment and subsequent embodiments is that the Center Section can articulate with respect to either the Main Section, the Broach Section or both. An advantageous feature of this articulation in combination with the bends of the Main, Center and Broach Sections is that Main Section can be offset spatially from the Broach Section yet maintain parallel along the longitudinal axes (a-a and b-b of FIG. 1. Although not depicted in subsequent embodiments, longitudinal axes a-a and b-b are similarly applicable in the subsequent embodiments. FIGS. 48A-48E depict multiple configurations of the present invention using embodiment 3 structure. Although said configurations are shown depicting Embodiment 3 of the present invention, they are equally applicable to the other embodiments described herein, including Embodiment 1.) The amount of offset or spatial separation between the Main Section and the Broach Section may be adjusted by the amount of articulation (rotation) between the Main Section and the Center Section and/or the Center Section and the Broach Section. This offset is desirable depending on the physical features of the patient. That is, for a slender patient undergoing hip replacement surgery the surgeon does not require as much offset as for a patient who is more rotund about the midsection and hip area. By maintaining parallel but spatially offset longitudinal axes between the Main Section and the Broach Section, the force delivered by the surgeon onto the Force Disc is transmitted in the same linear direction onto the Broach Section and ultimately the Broach.

Another beneficial feature of the articulating joints of the present invention is that the Broach Handle 1000 may be used for either a left or right hip replacement. By articulating the joints between the Main, Center and Broach sections, a surgeon can convert the handle from a Right Broach Instrument to a Left Broach Instrument or vice versa.

The aspects and embodiments of the present invention provide a method for improving the preparation of the bone for example the femur in a hip replacement surgery. The articulating broach handle allows for quick and simple adjustments to the broach handle to accommodate for whether the surgeon is performing a right hip replacement or a left hip replacement, and the physical stature of the patient (protruding midsection or not). Articulating the first mechanical coupling 1010 and the second mechanical coupling 1020 allows a surgeon to vary the offset the Main Section 1200 from the Broach Section 1400. By employing an embodiment of the present invention, the surgeon need only use one articulating broach handle 1000 instead of having to choose from a multitude of broach handles.

Depending on the amount of offset required, the surgeon will activate one or both of the Triggers 1500A, 1500B. If the upper trigger 1500A is activated, the slant surface 1573 moves transfer rod 1210 distally which acts upon the proximal end 1231 of the first connector. This action causes the first connector 1230 to move distally within cavity 1266, separating the Center Section from the Main Section. Once the two sections are sufficiently separated (i.e., depth of the gears) the trapezoid-shaped gear teeth 1281, 1384 are disengaged from each other allowing the surgeon to articulate the first mechanical coupling 1010 a full 360 degrees or a subset thereof in 24 degree increments, depending on the number of cooperating gear teeth. Once the desired offset of the first mechanical coupling 1010 is achieved, the surgeon releases the top trigger 1500A causing the distal end 1280 of the Main Section and proximal end 1350 of the Center Section to re-engage as a result of spring 1240. That is, when transfer rod 1210 acts on the first connector 1230 moving it distally, spring 1240 is compressed. Once the pressure is released on the first connector 1230 as a result of the upper trigger 1500A being released, spring 1240 is allowed to expand causing the first connector 1230 to move in a proximal direction within cavity 1266 and the trapezoid-shape gear teeth 1281, 1384 re-engage, locking the first mechanical coupling in place.

If the bottom trigger 1500B is activated, the surgeon is able to articulate the second mechanical coupling between the Broach Section 1400 and the Center Section 1500. By activating the lower trigger 1500B the slant surface 1573 moves transfer rod 1220 distally which acts upon the engagement pin 1250. This action causes the engagement pin 1250 to move distally acting on transfer rod 1310 which acts upon the proximal end 1331 of the second connector 1330. By moving the second connector distally, the Broach Section 1400 separates from the Center Section 1300. Once the two sections are sufficiently separated (i.e., depth of the gears) the trapezoid-shaped gear teeth are disengaged from each other allowing the surgeon to articulate the second mechanical coupling 1020 a full 360 degrees or a subset thereof in 24 degree increments. Once the desired offset of the second mechanical coupling 1020 is achieved, the surgeon releases the bottom trigger 1500B causing the distal end 1360 of the Center Section and the proximal end of the Broach Section to re-engage as a result of spring 1320. That is, when transfer rod 1310 acts on the second connector 1330 moving it distally, spring 1320 is compressed. Once the pressure is released on the second connector 1330 as a result of the bottom trigger 1500B being released, spring 1320 is allowed to expand causing the second connector 1330 to move in a proximal direction within cavity 1362 and the trapezoid-shape gear teeth re-engage, locking the second mechanical coupling 1020 in place.

The Broach Section 1400 allows for the use of various broaches, depending on the situation and size.

Embodiment 2

Figure 28:
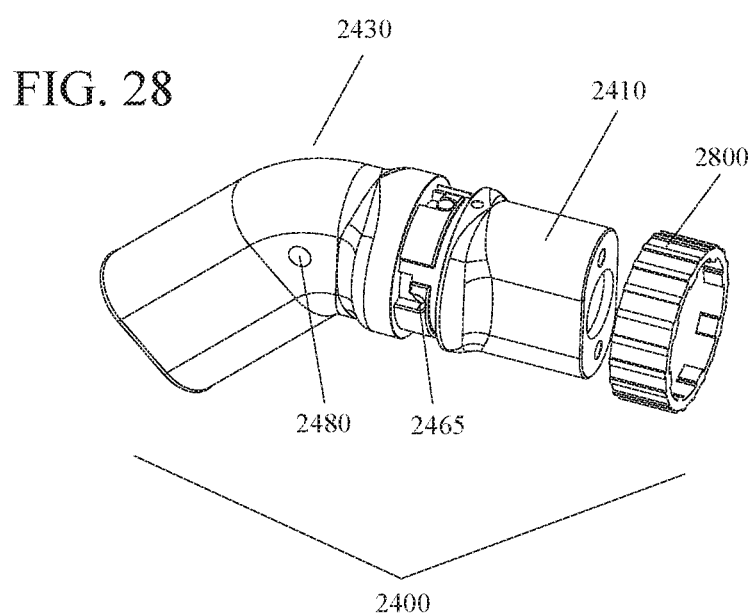
FIG. 28 is an exploded view of a 180 Joint of the embodiment depicted in FIG. 12.

FIGS. 12, 13A, 13B and 14A depict a second embodiment of the articulating broach handle 2000 of this invention. Articulating broach handle 2000 includes 4 sections with 3 joints allowing articulation of the various sections. In the example described, 2 joints articulate in 45 degree increments and one joint articulates in 90 degree increments. It is understood that the amount of articulation per joint can vary. The broach handle from the proximal end to the distal end consists of a Force Disc 2100, a Main Section 2200, a First Connector Lock Sleeve 2600, a Center Section 2300, a Junction 2 2900, a Second Connector Lock Sleeve 2700, a 180 Joint 2400 (FIG. 28), a Third Connector Lock Sleeve 2800 and a Broach Section 2500. The Main and Center sections may be constructed in two mirrored halves, top (a) and bottom (b) halves or as a single structure. The halves may be semi-permanent or permanently affixed together. Semi-permanent attachment of the mirrored halves (sections) allow for disassembly. Each section is substantially solid.

Broach Handle 2000 allows for 360 degree rotation of parts of the Broach Handle with respect to each part in varying amounts of increments. Although the embodiment of the Broach Handle as described below consists of three articulating joints, the Broach Handle may comprise more or less articulating joints as necessary. Embodiment 1 described above comprises two articulating joints. Also, as discussed below, the amount of rotation per increment may be varied by the construction of each joints. In the embodiment of Embodiment 2, the first and second articulating joints may be rotated in 45 degree increments and the third articulating joint may be rotated in 90 degree increments. Each joint can be rotated a full 360 degrees in either clockwise or counterclockwise directions.

The proximal end of the Broach Handle 2000 comprises a circular shaped Force Disc 2100 the same or similar as in Embodiment 1 (FIGS. 3A, 3B). The proximal end 2270 of the Main Section 2200 is assembled with the Force Disc 2100 may be permanently or semi-permanently attached together by a weld or known fixation methods.

Figure 15:
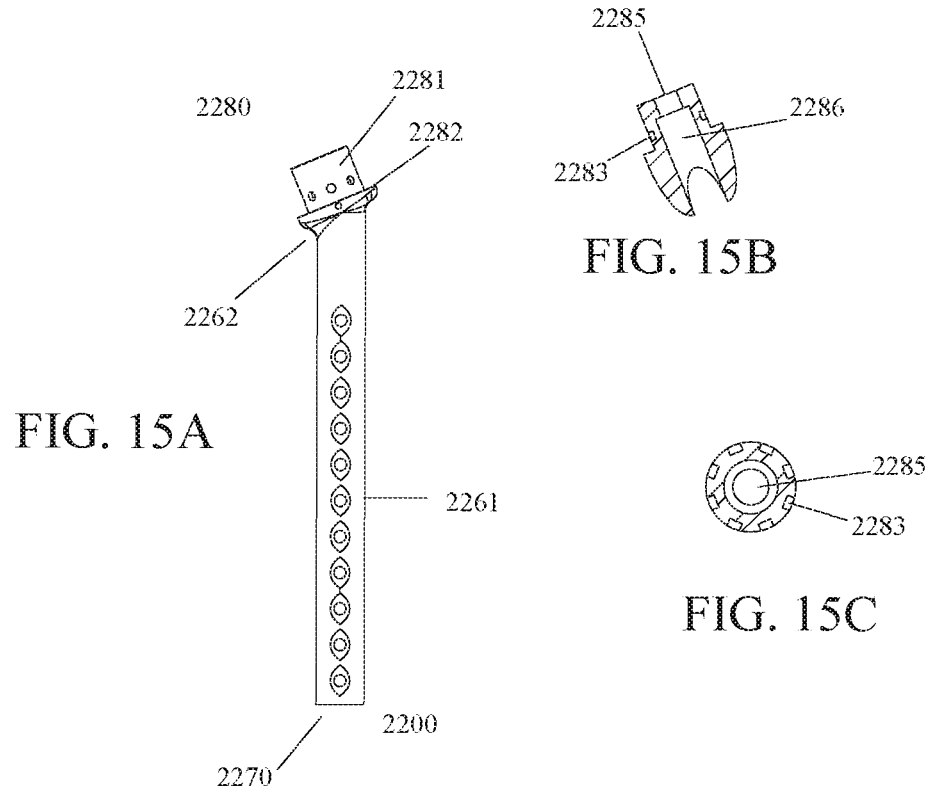
FIG. 15A is a front view of a Main Section of the embodiment depicted in FIG. 12.
FIG. 15B is cross-sectional view of the Main Section of the embodiment depicted in FIG. 12.
FIG. 15C is a cross-sectional view of a section of the Main Section of the embodiment depicted in FIG. 12.
Figure 16:
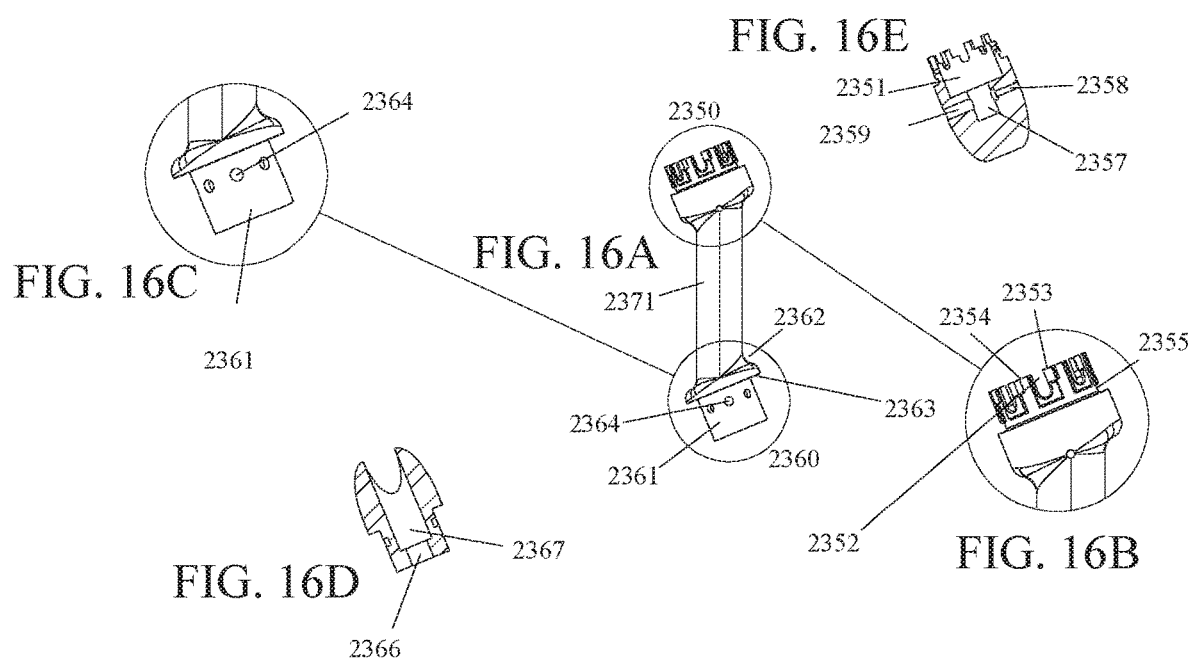
FIG. 16A is a front view of a Center Section of the embodiment depicted in FIG. 12.
FIG. 16B is an enlarged view of the proximal end of the Center Section of the embodiment depicted in FIG. 12.
FIG. 16C is a top view of the distal end of the Center Section of the embodiment depicted in FIG. 12.
FIG. 16D is a cross-sectional view of the proximal end of the Center Section of the embodiment depicted in FIG. 12.
FIG. 16E is a cross-sectional view of the distal end of the Center Section of the embodiment depicted in FIG. 12.

The Main Section 2200 (FIGS. 15A-C) is a longitudinal linear shaft 2261 with a bend (2262) at the distal end 2280.

The bend 2262 is preferably between 50 and 80 degrees, and more preferably 67.5 degrees. The length of the Main Section 2200 is approximately 5.7 inches. The width of the Main Section 2200 is approximately 0.5 inches and has a height of approximately 0.4375 inches along the longitudinal linear shaft 2261. A Main Slip Fit Shaft 2281 at the distal end 2280 of the Main Section 2200 at the bend 2262 and beyond in the distal direction is cylindrical. The diameter of the Main Slip Fit Shaft is approximately 0.6250 inches. The diameter of the Main Slip Fit Shaft is smaller than the diameter of the bend creating a first ledge 2282.

Figure 17:
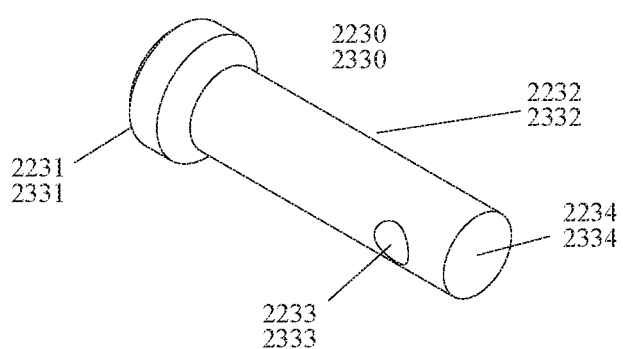
FIG. 17 is a perspective view of a Joint Connector of the embodiment depicted in FIG. 13A.

The perimeter of the Main Slip Fit Shaft 2281 at the distal end 2280 of the Main Section 2200 includes 8 evenly spaced (45 degrees apart) bores 2283 to secure 8 lock pins 2284. The distal end of the Main Slip Fit Shaft 2281 includes a Main Bore 2285 and a Main Spring Pocket 2286 to house the First Joint Connector 2230 (FIG. 17) and First Joint Spring 2240. The First Joint Connector 2230 is cylindrical in shape. The proximal end 2231 diameter is larger than the shaft 2232 of the First Joint Connector. Near the distal end 2234 is a bore 2233, perpendicular to the shaft. The First Joint Connector connects the Main Section 2200 and the Center Section 2300. The Main Spring Pocket 2286 is sized to allow the First Joint Connector 2230 to move proximally when a user applies a linear force to the Main Section in the proximal direction.

Encircling the proximal end 2231 of the First Joint Connector 2230 within the mid-section 2233 is a First Joint Spring 2240 which is housed in the Main Spring Pocket 2286 at the distal end 2280 of the Main Section 2200.

The Center Section 2300 (FIGS. 16A-E) of this embodiment of the Broach Handle 2000 interconnects the Main Section 2200 and the Junction J2 2900. The Center Section 2300 comprises a proximal end 2350 which is angled at 67.5 degrees from the center shaft 2371 and a distal end 2360 which is angled at 67.5 degrees in the opposite direction.

The proximal end 2350 is approximately 0.775 inches in length, the center shaft 2371 is approximately 2.3512 inches in length, and the distal end 2360 is approximately 0.497 inches length for a total length (taking into consideration the offset angles of both the proximal and distal ends) of 3.6752 inches.

The proximal end 2350 of the Center Section 2300 comprises an eight prong circlet 2351 having eight locating slots 2352 coincident with eight mating surfaces 2353. The eight locating slots 2352 extend further distally than the eight mating surfaces 2353, allowing the eight lock pins 2284 of the Main Section 2200 to rest below the mating surfaces (see FIG. 14B). The number of prongs of the circlet corresponds to the number of locking pins.

Using an eight prong circlet with eight locking pins allows for a 45 degree incremental change in articulation. Increasing the number of pins and prongs will reduce the incremental size. Whereas, fewer pins and prongs increase the size of the incremental change. It is anticipated that the incremental size change may range from 10 degrees to 90 degrees. Although, smaller and larger incremental change in articulation is contemplated.

The inner diameter of the circlet 2351 is sized to mate with the Main Slip Fit Shaft 2281. The proximal end 2350 of the Center Section 2300 includes a Bore 2351 and a Pocket 2357 sized and shaped to receive the distal end 2234 of the First Joint Connector 2230. The First Joint Connector 2230 is firmly seated within this Pocket 2357 such that there is no movement between the First Joint Connector and the Center Section 2300. The First Joint Connector is secured to the proximal end of the Center Section by a Lock Dowel 2359 located distal to the eight prong circlet which extends through the bore 2233 of the First Joint Connector. A Knock Out Hole 2358 is located on the opposite side of the Dowel 2359, allowing means to remove the Dowel from the Center Section. The First Joint Spring 2240, housed in the Main Spring Pocket 2286, encircles the midsection 2232 of the First Joint Connector 2230 such that the First Joint Spring 2240 movably connects the Center Section 2300 to the Main Section 2200. The distal end of the Main Section and the proximal end of the Center Section form a First Articulating Joint AJ1 (FIG. 14B), allowing the sections to articulate in 45 degree increments.

Figure 19B:
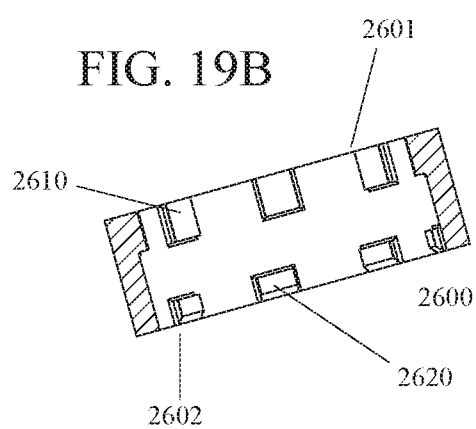
FIG. 19B is a cross-sectional view of the First Connector Lock Sleeve of the embodiment depicted in FIG. 12.
Figure 19A:
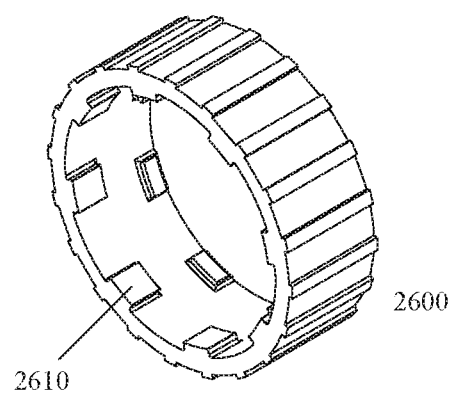
FIG. 19A is a perspective view of a First Connector Lock Sleeve of the embodiment depicted in FIG. 12.

A First Connector Lock Sleeve 2600 (FIGS. 19A-B) encircles the distal end 2280 of the Main Section 2200 and the proximal end 2350 of the Center Section 2300. The First Connector Lock Sleeve functions to lock the lock pins 2284 into the locating slots 2352. The interior surface of the First Connector Lock Sleeve includes 2 sets of 8 teeth (2610, 2620). The set of teeth 2610 at the proximal end 2601 of the First Connector Lock Sleeve 2600 are sized and shaped to fit between the prongs 2354 of the circlet 2351 and rest on the mating surfaces 2353 allowing the First Connector Lock Sleeve to rotate in a clockwise direction to lock the lock pins 2284 of the Main Section 2200 into the locating slots 2352 of the Center Section 2300. The number of teeth 2610, 2620 corresponds to the number of prongs and locking pins.

A second set of shorter teeth 2620 are located at the distal end 2602 of the First Connector Lock Sleeve 2600 are laterally offset from the first set of teeth 2610 at the proximal end of the First Connector Lock Sleeve 2600. The second set of teeth 2620 fit into a groove 2355 (FIG. 16B) distally from the locating slots 2352 of the Center Section 2300 such that the when the First Connector Lock Sleeve 2600 is rotated clockwise the First Connector Lock Sleeve is prevented from moving in the proximal direction when a force acts upon the First Connector Lock Sleeve 2600.

The length of the First Connector Lock Sleeve 2600 prevents the Sleeve from rotating counterclockwise to an unlock position because the First Connector Lock Sleeve is "pinched" between the Main and Center Sections due to the force of the First Connector Spring 2240.

The distal end 2360 of the Center Section 2300 has the same geometry as the distal end 2280 of the Main Section 2200. That is, a Center Slip Fit Shaft 2361 at the distal end 2360 of the Center Section 2300 at the bend 2362 and beyond in the distal direction is cylindrical. The diameter of the Center Slip Fit Shaft 2361 is approximately 0.6250 inches. The diameter of the Center Slip Fit Shaft is smaller than the diameter of the bend 2362 creating a ledge 2363.

Figure 18:
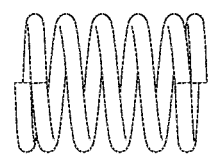
FIG. 18 is a front view of a Joint Spring of the embodiment depicted in FIG. 13A.

The perimeter of the Center Slip Fit Shaft 2361 includes 8 evenly spaced (45 degrees apart) bores 2364 to secure 8 lock pins 2365. The distal end of the Center Slip Fit Shaft 2361 includes a Center Bore 2366 and a Center Spring Pocket 2367 to house the Second Joint Connector 2330 (FIG. 17) and Second Joint Spring 2340 (FIG. 18). The Second Joint Connector is sized and shaped the same as the First Joint Connector 2230 and connects the Center Section 2300 and the Junction J2 2900. The Second Joint Connector 2330 is cylindrical in shape. The proximal end 2331 diameter is larger than the shaft 2332 of the First Joint Connector. Near the distal end 2334 is a bore 2333, perpendicular to the shaft. The Second Joint Connector 2330 is held in place by Lock Dowel 2935 near bend 2390. The Lock Dowel extends through the bore 2333 of the Second Joint Connector holding the Second Joint Connector to Junction J2 2900. The Center Spring Pocket 2367 is sized to allow the Second Joint Connector 2330 to move proximally when a user applies a linear force to the Center Section 2300 in the proximal direction.

Encircling the proximal end of the Second Joint Connector 2330 within the mid-section 2332 is a Second Joint Spring 2340 which is housed in the Center Spring Pocket 3267 at the distal end 2360 of the Center Section 2300. The Second Joint Spring is sized and shaped the same as the First Joint Spring 2240 (FIG. 18). The Center Spring Pocket 2367 is sized to allow the Second Joint Connector 2330 to move proximally when a user applies a linear force to the Center Section in the proximal direction.

Figures 20A, 20B:
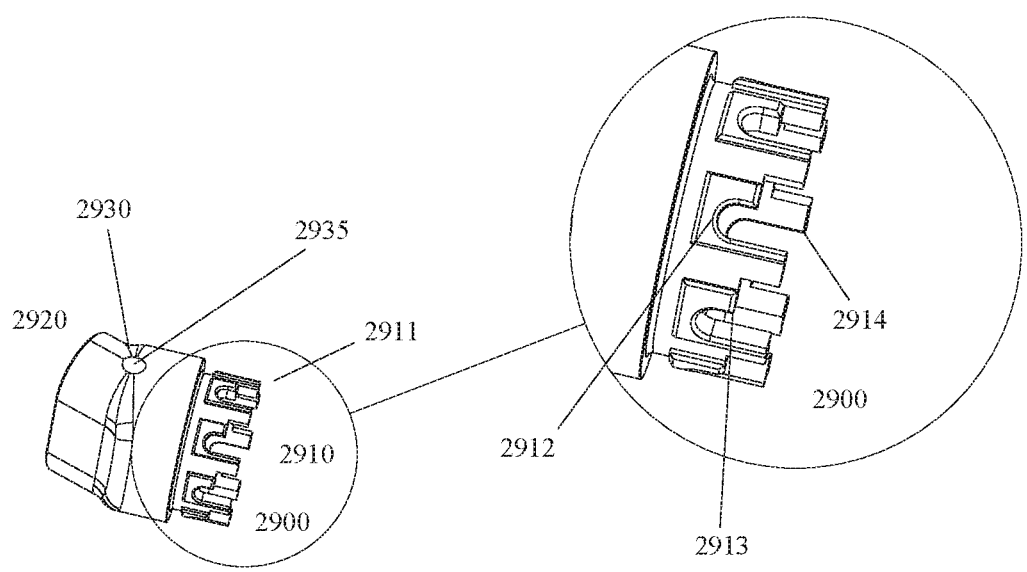
FIG. 20A is a perspective view of a J2 Section of the embodiment depicted in FIG. 12.
FIG. 20B is a perspective view of the proximal end of the J2 Section of the embodiment depicted in FIG. 12.

FIGS. 20A-B depict a Junction J2 2900 having a proximal end 2910 and a distal end 2920. The proximal end 2910 is similar to the proximal end 2350 of the Center Section 2300 having an 8 prong 2914 circlet 2911 comprising eight (8) locating slots 2912 and eight (8) mating surfaces 2913. The geometry of the locating slots 2912 of the Junction J2 circlet 2911 are identical to that of the Center Section circlet 2351. All other geometry of the Junction 2 circlet 2911 is opposite allowing for reverse rotational locking direction of the Second Connector Lock Sleeve 2700. That is, the 8 mating surfaces 2913 are on the opposite side of the locating slots 2912 as compared to the Center Section circlet 2351. The distal end of the Center Section and the proximal end of J2 forms a Second Articulating Joint AJ2 (FIG. 14C) allowing the sections to articulate in 45 degree increments.

Immediately distal of the proximal end 2910 is a bend 2930. The distal end 2920 of Junction J2 2900 is solid planar surface that is permanently (welded) or semi-permanently attached to the 180 Joint 2400.

Figure 21A:
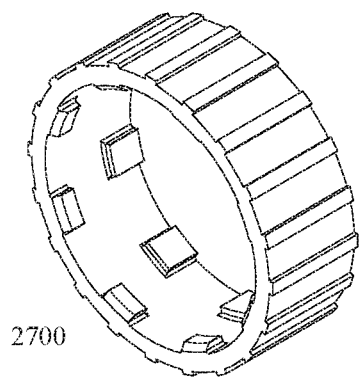
FIG. 21A is a perspective view of a Second Connector Lock Sleeve of the embodiment depicted in FIG. 12.
Figure 21B:
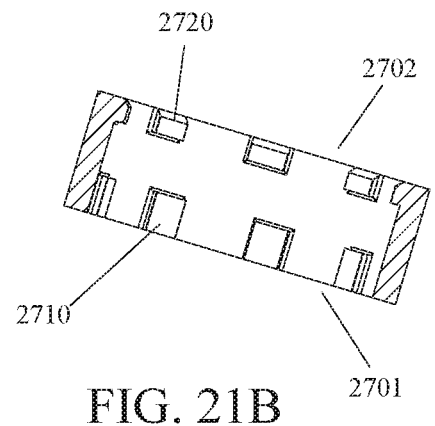
FIG. 21B is a cross-sectional view of the Second Connector Lock Sleeve of the embodiment depicted in FIG. 12.

Second Connector Lock Sleeve 2700 (FIGS. 21A-B) has similar geometry as First Connector Lock Sleeve 2600 and functions in a similar manner with the exception that the rotational locking direction of Second Connector Lock Sleeve is opposite than that of the First Connector Lock Sleeve. The interior surface of the Second Connector Lock Sleeve includes 2 sets of 8 teeth, 2710 at the proximal end 2701 and 2720 at the distal end 2702.

Designing the rotational locking direction of Second Connector Lock Sleeve 2700 opposite the First Connector Lock Sleeve 2600 allows for simultaneous locking and unlocking of the 2 joints by turning First Connector Lock Sleeve 2600 in the opposite direction as that for Second Connector Lock Sleeve 2700 using both hands at once, with each hand dedicated to a specific locking sleeve.

Figure 25:
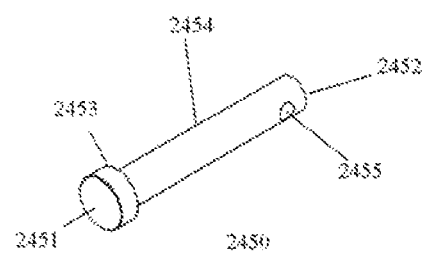
FIG. 25 is a perspective view of a 180 Pin of the embodiment depicted in FIG. 13A.

The 180 Joint 2400 allows a surgeon to rotate the Broach Section 2500 180 degrees transforming the Broach Handle 2000 from, for example, a Right Handle to a Left Handle, or vice versa. The 180 Joint comprises 2 main components, a 180 Pull 2410 (FIGS. 22A-C) and a 180 Junction 2430 (FIGS. 23A-D), that are movably connected to each other via 180 Pin 2450 (FIG. 25).

The 180 Pull 2410 (FIG. 22B) is approximately 1 inch in length. The proximal end 2411 is a planar surface that is semi-permanently or permanently affixed to the distal end of Junction J2 2900. Proximal end 2411 may be permanently affixed to the distal end of Junction J2 2900 by two locating dowels 2411-1 for welding. The distal end 2415 comprises a four (4) prong circlet 2418 similar in geometry as the 8 prong circlets 2351, 2911 of the proximal ends of the Center Section 2300 and Junction J2 2900. The distal end of the 180 Pull includes Mating Bore 2416 having diameter of approximately 0.625 inch and is sized to fit the 180 Junction Slip Fit Journal 2435. A two tiered center bore comprising a clearance bore 2413 and a Spring Pocket 2412 extends the length of the 180 Pull 2410. The diameter of the Spring Pocket 2412 is larger than the diameter of the clearance bore 2413. The Spring Pocket at the proximal end is sized to house the proximal end 2451 of 180 Pin 2450 and 180 Spring 2470.

The 180 Junction (FIGS. 23A-D) includes a distal end 2432 and a 135 degree bend 2433 near the proximal end 2431. Coincident with the 135 degree bend 2433 is a Pin Retaining Bore 2437 extending the width of the 180 Junction. The proximal end of the 180 Junction includes a Retaining Bore 2434 extending distally beyond the 135 degree bend. The Retaining Bore is sized to accept the distal end 2452 of the 180 Pin 2450. The proximal end 2421 of the 180 Junction is cylindrical and includes a 180 Junction Slip Fit Journal 2435 having four (4) bores 2436 to secure four (4) lock pins 2465 (FIG. 13A) which are pressed fit into the bores of the 180 Junction Slip Fit Journal to engage the four (4) locking slots 2417 of the 180 Pull 2410. The 180 Junction Slip Fit Journal 2435 and the 4 prong circlet 2418 function in a similar manner as the distal end of the Main Section and the proximal end of the Center Section.

Figure 26:
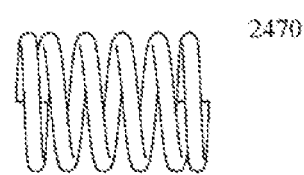
FIG. 26 is a perspective view of a 180 Spring of the embodiment depicted in FIG. 13A.

The 180 Pin 2450 (FIG. 25) includes a Thrust Face 2453 for the 180 Spring 2470 (FIG. 26) at the proximal end 2451 which has a greater diameter than the Shaft 2454. The Thrust Face diameter is compatible with the Spring Pocket 2412 dimensions at the proximal end of the 180 Pull 2410. Whereas, the diameter of the Shaft 2454 is compatible with the Clearance Bore 2413 of the 180 Pull and the Retaining Bore 2434 at the proximal end of the 180 Junction. The distal end 2452 of the 180 Pin 2450 includes a bore 2455 that is perpendicular direction to the proximal-distal direction.

Figure 24:
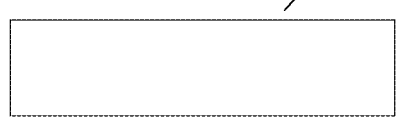
FIG. 24 is a side view of a 180 Retaining Dowel of the embodiment depicted in FIG. 12.

The 180 Junction 2430 is assembled such that the 180 Pin 2450 and 180 Spring 2470 which surround the shaft 2454 of the 180 Pin 2450 are inserted distally through the Spring Pocket 2412 of the 180 Pull starting at the proximal end 2411 of the 180 Pull 2410. The distal end 2452 of the 180 Pin 2450 is extended through the Retaining Bore 2434 of the 180 Junction 2430 such that Bore 2455 of the 180 Pin 2450 is aligned with the Pin Retaining Bore 2437 of the 180 Junction. A 180 Retaining Dowel 2480 (FIG. 24) is inserted through the Pin Retaining Bore 2437 and the 180 Pin Bore 2455 such that the 180 Pin is securely fitted to the 180 Junction.

Figure 14:
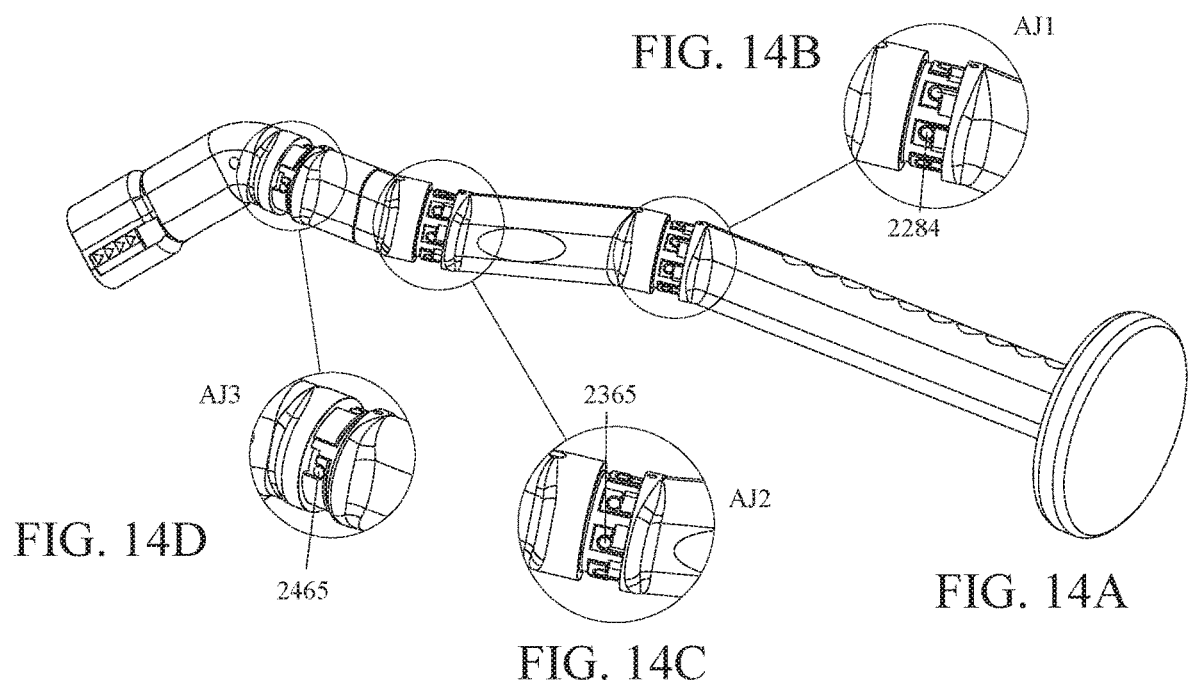
FIG. 14A is an exposed view of the articulating mechanisms of the embodiment depicted in FIG. 12.
FIG. 14B is an isolated view of the articulating mechanism of a first joint of the embodiment depicted in FIG. 12.
FIG. 14C is an isolated view of the articulating mechanism of a second joint of the embodiment depicted in FIG. 12.
FIG. 14D is an isolated view of the articulating mechanism of a third joint of the embodiment depicted in FIG. 12.

The distal end of the 180 Pull and the proximal end of the 180 Junction 2430 form a Third Articulating Joint AJ3 (FIG. 14D). That is the 180 Pull is able to rotate with respect to the 180 Junction, permitting four (4) articulating positions in 90 degree increments.

Figure 27A:
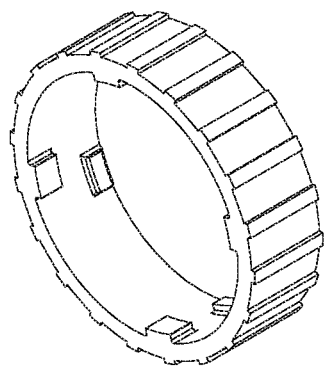
FIG. 27A is a perspective view of a Third Connector Lock Sleeve of the embodiment depicted in FIG. 12.
Figure 27B:
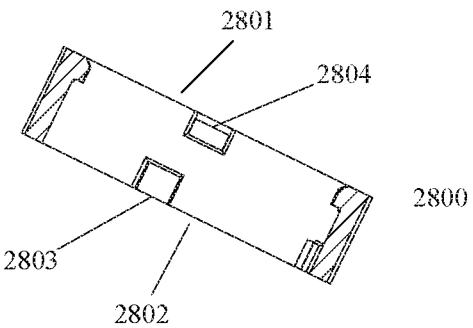
FIG. 27B is a cross-sectional view of the Third Connector Lock Sleeve of the embodiment depicted in FIG. 12.

A Third Connector Lock Sleeve 2800 (FIGS. 27A-B) encircles the distal end 2415 of the 180 Pull and the proximal end of the 180 Junction. The Third Connector Lock Sleeve functions to lock the lock pins 2465 into the locating slots 2417. The Third Connector Lock Sleeve functions similar to that of the First Connector Lock Sleeve 2300 except that the Third Connector Lock Sleeve has two (2) sets of four (4) teeth. The set of teeth 2804 at the proximal end 2801 of the Third Connector Lock Sleeve are sized and shaped to fit into a groove 2419 on the 180 Pull. Whereas the longer set of teeth 2803 located at the distal end 2802 are sized and shaped to rotate to a position either in front of the four lock pins 2465 or away from the lock pins.

The length of the Third Connector Lock Sleeve 2800 controls the sleeve from rotating by being pinched between the 180 Junction and 180 Pull joint faces.

While it is described that the First and Second Articulating Joints can be rotated in 45 degree increments, it is contemplated that these joints may have more or less lock pins and locating slots allowing for differing amounts of rotation per increment. Additional pins and locating slots, beyond eight (8) will reduce the amount of rotation per increment. Conversely, less pins and locating slots than the eight (8) described will increase the amount of rotation per increment.

This is similar for the Third Articulating Joint AJ3 which the described embodiment includes 4 lock pins and locating slots. Additional or fewer lock pins and locating slots will affect the amount of rotation per increment. For the Third Articulating Joint, it is contemplated that the minimum number of lock pins and locating slots will be two (2). This allows for 180 degrees of rotation per increment.

The Broach Section 2500 (FIG. 13C) of the Broach Handle 2000 allows for the easy and fast connection of a broach to the Broach Handle. The broach section engaging mechanism allows for a reliably secure attachment preventing the broach from rotating about its shaft (i.e., its longitudinal axis) when engaged with the Broach Section. Although the broach section engaging mechanism described below is used to connect a broach with the Broach Handle, the engaging mechanism may be used in other environments for rapidly connecting and disconnecting two devices and ensuring the devices are firmly and securely engaged.

The Broach Section interconnects the 180 Joint with the distal end a Broach. The proximal end 2510 the Broach Section attaches to the 180 Junction 2430 either semi-permanently or permanently via a weld or some other means of affixing the two sections. The Broach Section comprises top and bottom halves (2505, 2501) along the longitudinal length. The Broach Section 2500 also includes a Pillow Block 2550 (FIGS. 31A-D), a Pillow Spring (2580 (FIG. 32), a Slide Release 2530 (FIGS. 33A-C), a Release Spring 2590 (FIG. 32) and a Locating Dowel 2595 (not shown).

Figure 30B:
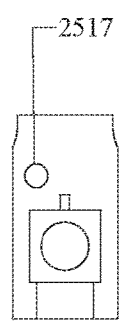
FIG. 30B is a cross-sectional top view of the bottom half of the Broach Section of the embodiment depicted in FIG. 12.
Figure 30C:
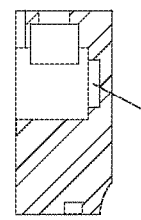
FIG. 30C is a cross-sectional side view of the bottom half of the Broach Section of the embodiment depicted in FIG. 12.
Figure 30A:
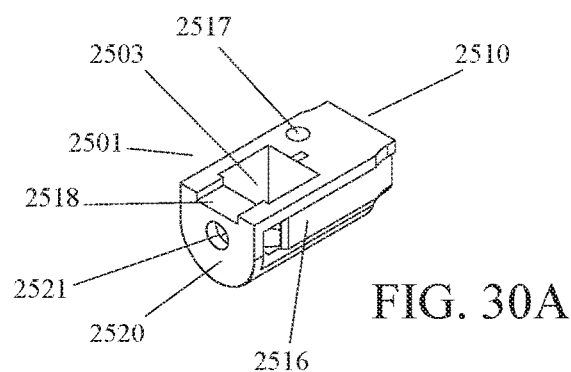
FIG. 30A is a perspective view of the bottom half of the Broach Section of the embodiment depicted in FIG. 12.

Both the top half 2505 (FIGS. 29A-D) and bottom half 2501 (FIGS. 30A-C) of the Broach Section have convex top and bottom surfaces, respectively and planar side surfaces similar to the Main Section, Center Section and 180 Junction section. The height of the Broach section is greater than that of the other sections of the Broach Handle.

The distal end 2506 of the top half has a slip fit bore 2507 to receive the Broach Shaft of the Broach (not shown). The slip fit bore 2507 ends into the top half of a Pillow Block Pocket 2503 which is formed when the top and bottom halves of the Broach Section are welded together. The top half of the Pillow Block Pocket 2503 formed in the top half has a notch 2504 at the proximal end 2508 allowing the radial male extension of the Broach Shaft to seat within the Pillow Block Pocket 2503 with the Pillow Block 2550. The bottom surface of the top halve includes a male guide 2509 that is used for alignment purposes when fitted with the bottom half 2501. The top half 2505, near the proximal end includes a bore 2511 for a dowel 2595 used during assembly of the top and bottom halves to align the two halves. Radii surfaces 2512 on the inner wall of the Pillow Block Pocket 2503 are stops for the Pillow Block 2550 such that the Pillow Block is held firmly against these surfaces before attaching a Broach by way of the Pillow Spring 2580.

The bottom half 2501 of the Broach Section includes the bottom half of the Slip Fit Pocket for the Pillow Block, a First Thrust Face 2513 (Clearance Bore) at the bottom of the Pillow Block Pocket maintains the position of the Pillow Spring 2580 and a Slide Release Pocket and Channel 2516 on one side of the bottom half. The distal end 2520 of the bottom half includes a Slip Fit Bore 2521 for the Slide Release 2530. The Slide Release Pocket and Channel 2516 extends from the proximal end 2510 to almost the distal end 2520 of the bottom half.

The bottom half 2501 also includes a dowel hole 2517 near the proximal end, similar to the top half for aligning the two halves during assembly. Reciprocal to male guide 2509 on the top half, the bottom half includes an indentation 2518 sized and shaped to fit the male guide 2509 which are used for alignment purposes.

Figure 32:
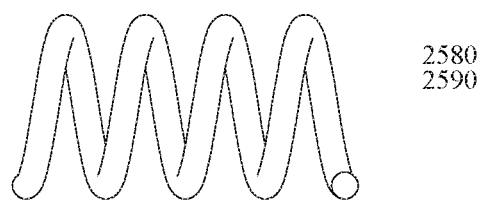
FIG. 32 is a side view of a Pillow Spring/Release Spring of the embodiment depicted in FIG. 13A.

The Slide Release 2530 (FIG. 33A-C) is L-shaped. The stem 2531 of the Slide Release includes three-dimensional directional arrows 2536, while the leg 2532 of the Slide Release includes a Slide Release Pin 2533 that mates concentrically with the Slip Fit Bore 2521 of the bottom half 2501. The Slide Release Pin 2533 when seated in the bottom half of the Broach Section will extend beyond the distal end of the Broach Section to seat within a reciprocal bore of the Broach. This feature restricts the Broach from rotating about its shaft axis. The opposite (internal) side of the leg of the Slip Release 2530 a Second Thrust Face 2534 and indentation 2535 to align the Release Spring 2590 (FIG. 32). The Release Spring applies constant force to the Slide Release 2530 and Pillow Block 2550. The Release Spring engages and disengages the Slide Release Pin 2533 which controls the Broach rotation. The Release Spring must be engaged when the Broach is in use to stop the Broach from rotating about the Broach shaft.

The Pillow Block 2550 (FIGS. 31A-D) is a substantially rectangular block. The geometry of the top surface 2551 is complementary to the Broach scallop on the Broach Shaft and allows for a solid connection of the Broach to the Broach Section 2500. The distal face 2552 includes a vertical channel 2553 (indentation) that acts as a thrust face for the Release Spring 2590. The bottom (underside) 2554 of the Pillow Block 2550 includes a Pillow Spring Clearance Pocket 2555 such that the Pillow Spring 2580 is secured by the First Thrust Face 2513 of the bottom half and the Pillow Block Pocket 2503. The Pillow Spring 2580 applies constant pressure to the Pillow Block 2550 ensuring lock engagement when a Broach is in use. The base of the Pillow Spring is thrust against the bottom half of the Broach and the top of the Pillow Spring is thrust against the upper face 2558 of Pillow Spring Clearance Pocket 2555.

The top 2551 of the Pillow Block 2550 includes a sloping concave top surface such that the proximal end 2556 of the top surface is higher than the distal end 2552. The width of the concave surface at the distal end 2552 is wider than at the proximal end 2556. At the proximal end of the top surface is a Locking Arc 2556. This surface, Locking Arc, engages with the radial notch on the Broach Shaft. This connection between the surfaces along with the upward pressure of the Pillow Spring 2580 stops any lateral movement of the Broach, keeping it locked in place. The lateral surfaces of the top of the Pillow Block form two (2) Side Stop Arcs 2557 are nested against two (2) equally arced surfaces (Radii Surfaces) 2512 on the top half of the Broach Section. The Side Stop Arcs 2557 restrict the return height within the top half of the Broach, ensuring that there are no obstructions or interference when the Broach Shaft is inserted. The geometry of the top surface mimics the receiving broach outer shaft diameter and allows for connection of the Broach. As the Broach Shaft is inserted into the Slip Fit Bore 2507 it forces the Pillow Spring 2580 to compress until the radial notch of the Broach Shaft is coincident with the Locking Arc 2556 and the Pillow Spring 2580 is compressed.

Similar to Embodiment 1, a unique feature of the present invention that the instrument can articulate with to the various sections comprising the instrument. An advantageous feature of this articulation in combination with the bends of the various sections allows for the Main Section to be offset spatially from the Broach Section yet maintain parallel longitudinal axes (a-a and b-b) FIGS. 34A-B. The amount of offset or spatial separation between the Main Section and the Broach Section may be adjusted by the amount of articulation (rotation) between the Main Section and Center Section, the Center Section and J2 Joint. This offset is desirable depending on the physical features of the patient. That is, for a slender patient undergoing hip replacement surgery the surgeon does not require as much offset as for a patient who is more rotund about the midsection and hip area. By maintaining parallel but spatially offset longitudinal axes between the Main Section and the Broach Section, the force delivered by the surgeon onto the Force Disc is transmitted in the same linear direction onto the Broach Section and ultimately the Broach.

Another beneficial feature is that the 180 Joint allows the surgeon to configure the instrument as either a Right or Left Instrument, depending on which hip is being replaced.

The aspects and embodiments of the present invention provide a method for improving the preparation of the bone for example the femur in a hip replacement surgery. As discussed, the articulating broach handle allows for quick and simple adjustments to the broach handle to accommodate for whether the surgeon is performing a right hip replacement or a left hip replacement, and the physical stature of the patient (protruding midsection or not).

Depending on if the surgeon will be performing a left hip or right hip replacement, the surgeon may need to articulate the Third Articulating Joint AJ3 to configure the Broach Handle as either a left or right handle. If it is necessary for the surgeon to articulate the Third Articulating Joint, the surgeon will first rotate the Third Locking Sleeve 2800 clockwise to release the lock pins 2465, allowing the surgeon to apply a linear force in the proximal direction to the 180 Pull. By pulling the 180 Pull towards the surgeon, the surgeon disengages the lock pins 2465 from the locating slots 2417. This allows the surgeon to articulate the 180 Junction in increments of 90 degrees to configure the Broach Handle as either a Left Handle or Right Handle. Once the desired configuration is achieved, the surgeon releases the 180 Pull and the 180 Pull moves distally due to the force in the compressed 180 Spring. The lock pins 2465 become seated in the locating slots 2417. The surgeon then rotates the Third Locking Sleeve 2800 counterclockwise such that the teeth 2803 are located directly in front of the lock pins 2465 preventing the lock pins from disengaging from the locating slots 2417. The Third Locking Sleeve 2800 is held in place because the Third Locking Sleeve is pinched in between the 180 Junction and 180 Pull due to the pressure of the 180 Spring exerting a distal force on the 180 Pull.

Depending on the amount of offset required due to the physical dimensions of the patient (large midsection or skinny), it may be necessary for the surgeon to articulate either or both of the First and Second Articulating Joints AJ1 and AJ2. The First and Second Articulating Joints functions similar to the Third Articulating Joint. To release the lock pins from the locating slots in the First Articulating Joint, the surgeon needs to rotate the First Connector Lock Sleeve in a counterclockwise direction. To secure the lock pins in the locating slots in the First Articulating Joint, the surgeon will rotate the First Connector Lock Sleeve clockwise until the set of eight (8) teeth are positioned directly in front of the locking pins. Similar to the Third Connector Lock Sleeve, the First Connector Lock Sleeve is pinched between the Main Section and the Center Section by the force of the First Joint Spring 2240 exerting on the Main Section 2200 in a distal direction towards the Center Section 2300.

As noted previously, the Second Articulating Joint AJ2 works in the opposite direction as that of the First Articulating Joint. That is, to unlocking the lock pins 2365, the Second Connector Lock Sleeve is rotated in a clockwise direction. To lock the lock pins 2365 in the locating slots 291, the surgeon will rotate the Second Connector Lock Sleeve in a counterclockwise direction.

Both the First and Second Articulating Joints in the above description can be rotated in 45 degree increments, in either direction. If addition lock pins are employed, the amount of rotation per increment decreases. Whereas, if the number of lock pins is less than eight, the amount of rotation per increment increases.

The Broach Section 2500 allows for the use of various broaches, depending on the situation and size. A surgeon may attach a Broach 1 (FIGS. 34A-C) prior to or after the surgeon has configuration the articulation of the three (3) articulating joints of the Broach Handle 2000.

The proximal end of the Broach 1 includes a shaft 1.1 having a scallop 1.2 contoured to mate with the Lock Arc 2556 of the Pillow Block 2550. The proximal end of the Broach also includes a Broach Bore. The Broach Bore is sized and shape to mate concentrically with the Slide Release Pin 2533 of the Broach Section. The mating of the Slide Release pin 2533 with the Broach Bore restricts the Broach 1 from rotating about its shaft axis.

A surgeon may attach the Broach 1 to the Broach Section 2500 by inserting the Broach Shaft 1.1 into the Slip Fit Bore 2507. As the Broach Shaft enters the Slip Fit Bore 2507 the Broach Shaft comes in contact with the convex top surface 2551 of the Pillow Block. Because of the sloping profile of the top surface 2551 and that the Pillow Block Spring 2580 forces the Pillow Block 2550 upwards, the further the Broach Shaft is inserted into the Slip Fit Bore it slides along the top surface 2551 forcing the Pillow Block down further into the Pillow Block Pocket 2503. This continues until the Broach Scallop 1.2 extends past the Lock Arc 2556 seating the Broach Shaft within the Broach Section 2500. To ensure proper installation, the Slide Release Pin 2533 mates with the Broach Bore at the distal end of the Broach. The Slide Release Spring 2590 acts on the Slide Release and in particular the Slide Release Pin distally to ensure the Slide Release Pin remains mated with the Broach Bore.

To remove the Broach from the Broach Section 2500, the surgeon will move the Slide Release 2530 proximally, compressing the Slide Release Spring and decoupling the Slide Release Pin 2533 from the Broach Bore. Once decoupled, the surgeon with rotate the Broach 1 either clockwise or counterclockwise such that the Slide Release Pin is no longer aligned with the Broach Bore. This rotation of the Broach will also disengage the Broach Shaft 1.2, and in particular the Broach Scallop, from the Lock Arc 2556 allowing the surgeon to distally remove the Broach 1 from the Broach Section.

Embodiment 3

Figure 35:
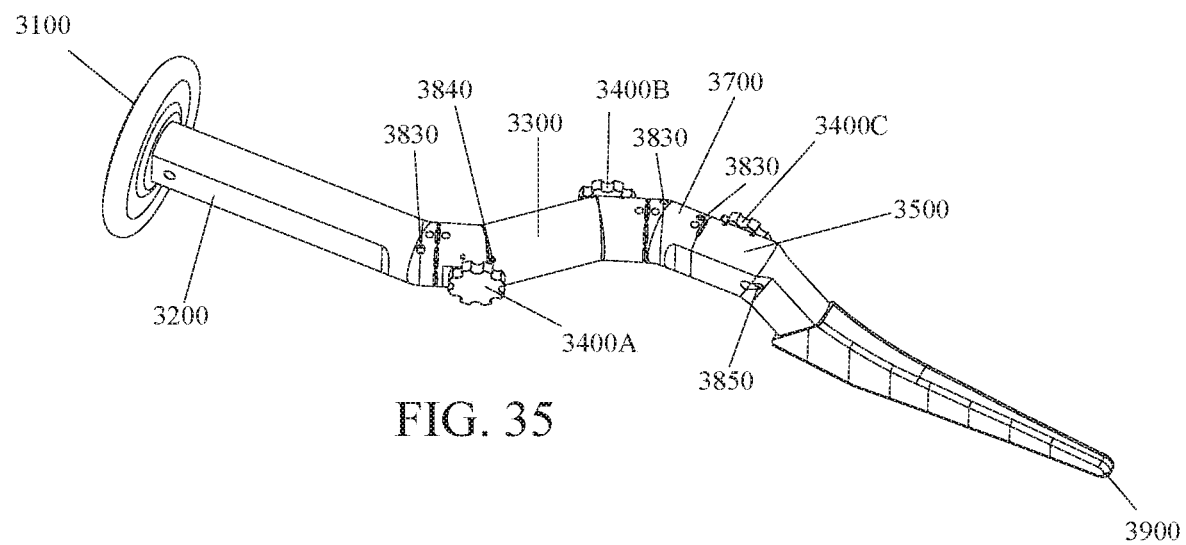
FIG. 35 is a perspective view of a preferred embodiment of an articulating broach handle.
Figures 36A, 36B, 36C:
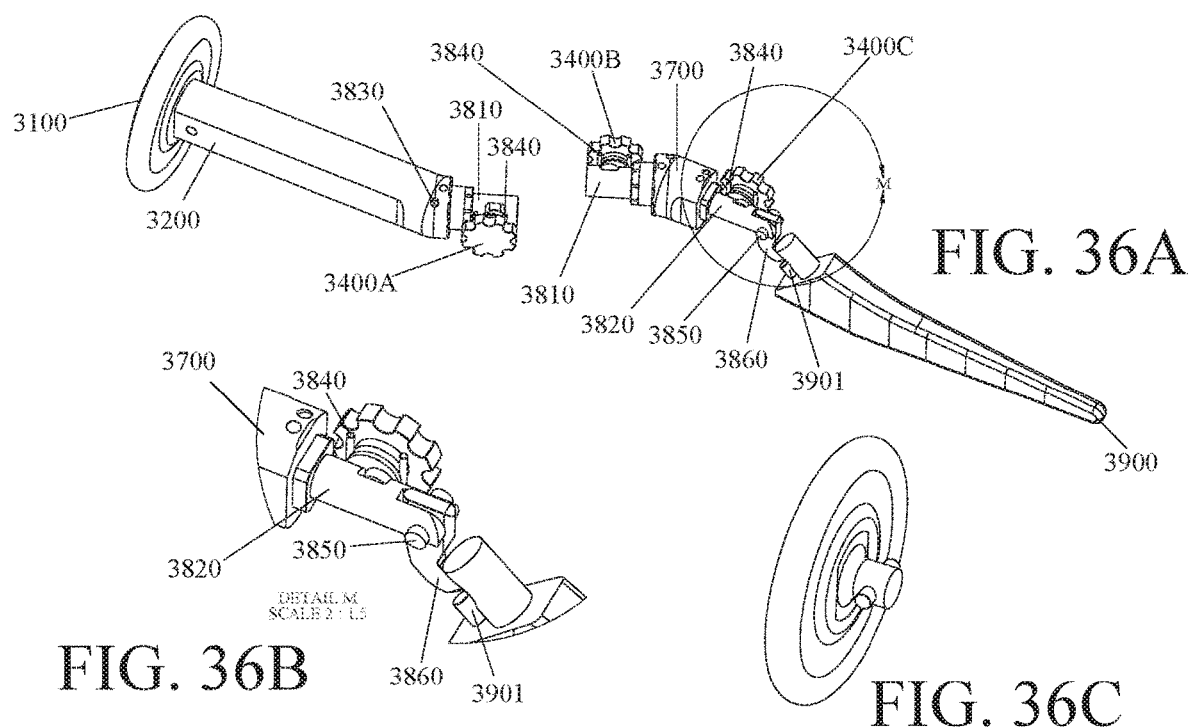
FIG. 36A is a cut-away view of the embodiment of the articulating broach handle of FIG. 35.
FIG. 36B is an exploded view of a section of the embodiment of the articulating broach handle of FIG. 35.
FIG. 36C is an exploded view of the Force Disc and attaching means to the Main Section of the embodiment of the articulating broach handle of FIG. 35.
Figure 39A:
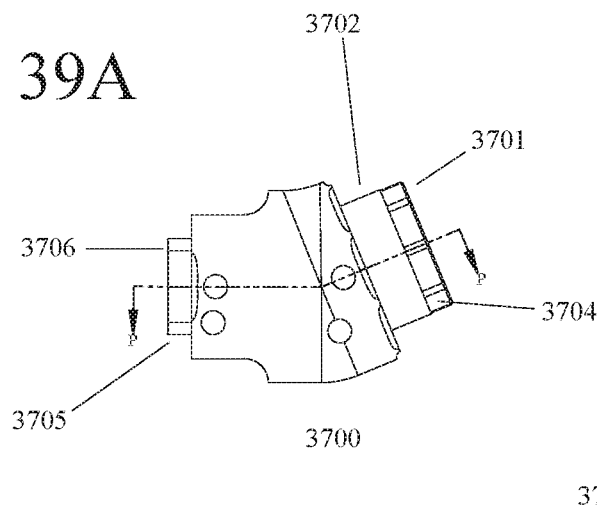
FIG. 39A is a perspective view of the Connecting Body of the embodiment of the articulating broach handle of FIG. 35.
Figure 39B:
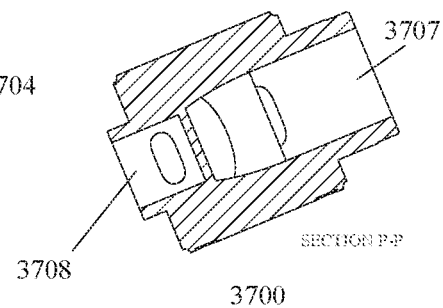
FIG. 39B is a cut-away view of the Connecting Body of FIG. 39A.
Figure 40A:
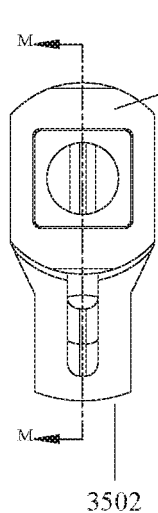
FIG. 40A is a front view of the Broach Section of the embodiment of the articulating broach handle of FIG. 35.
Figure 40B:
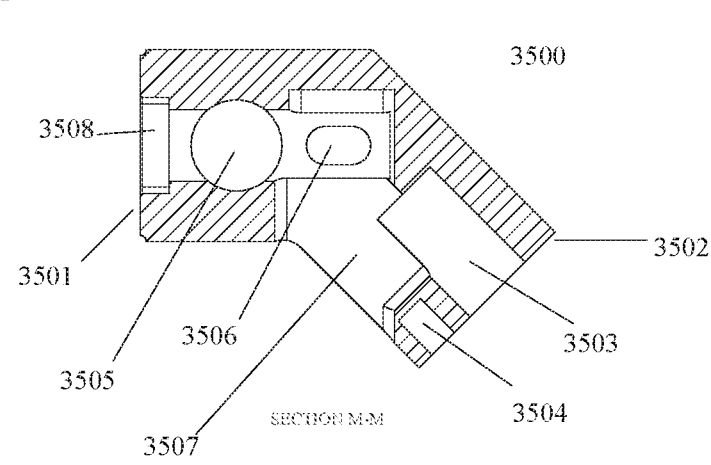
FIG. 40B is a cut-away view of the Broach Section of FIG. 40A.
Figure 41:
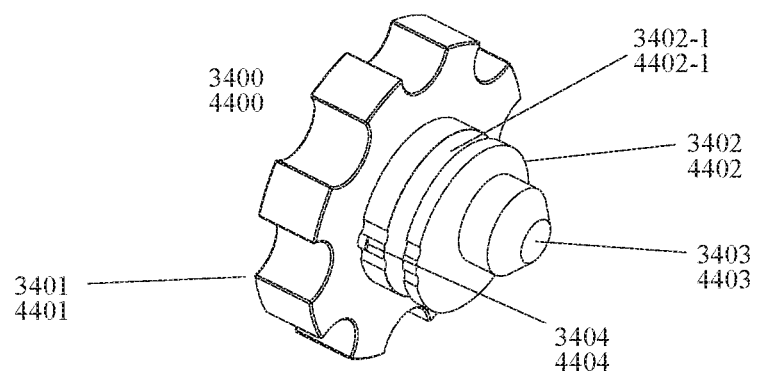
FIG. 41 is a perspective view of the Grip Cam of the embodiment of the articulating broach handle of FIG. 35.
Figure 45:
FIG. 45 is a perspective view of the Rod Spinlock Pin of the embodiment of the articulating broach handle of FIG. 35.
Figure 47:
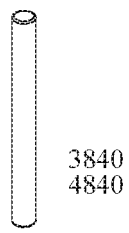
FIG. 47 is a perspective view of the Wheel Lock Pin of the embodiment of the articulating broach handle of FIG. 35.

FIGS. 35 and 36A, B depict a third embodiment of the present invention as described in the context of an articulating broach handle 3000. The articulating broach handle from the proximal end to the distal end consists of a Force Disc 3100, a Main Section 3200 (FIG. 37), a Center Section 3300 (FIGS. 38A, B), a Connecting Body 3700 (FIGS. 39A, B) and a Broach Section 3500 (FIGS. 40A, B). The Main Section and the Center Section may articulate with respect to one another via a cam mechanism consisting of a Grip Cam 3400A (FIG. 41), a Push Rod 3810 (FIG. 42), a Rod Spinlock Pin 3830 (FIG. 45) and two Wheel Secure Pins 3840 (FIG. 47). A similar cam mechanism, Grip Cam 3400B, allows articulation of the Center Section 3300 with respect to the Connecting Body 3700. A third cam mechanism, Grip Cam 3400C, a Clasp Rod 3820 (FIG. 43) and two Wheel Secure Pins 3840 allows a Broach 3900 to be releasably engaged with Broach Handle 3000.

The Force Disc 3100 is similar to and provides the same function as the Force Disc of Embodiments 1 and 2. FIG. 36C depicts an exploded view of the Force Disc which may be permanently affixed to the Main Section using a boss and retaining dowel, whereby the distal end of the boss in press fit into the proximal end of the Main Section and is secured by a dowel extending perpendicular to the shaft of the Main Section. This connection means of the Force Disc and Main Section is applicable to embodiments 2 and 4 of the present invention.

Figure 37:
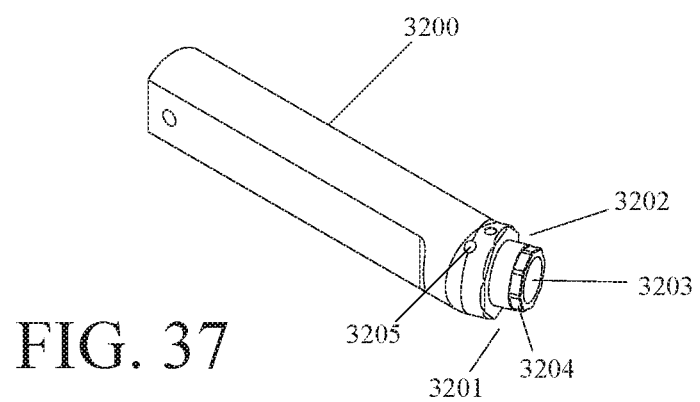
FIG. 37 is a perspective view of the Main Section of the embodiment of the articulating broach handle of FIG. 35.
Figure 42:
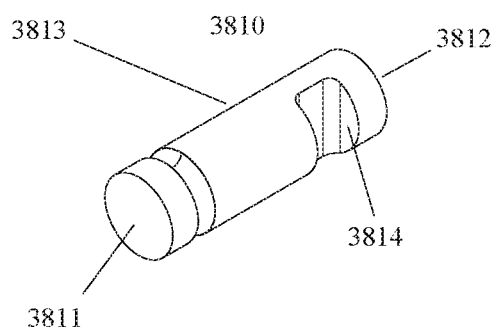
FIG. 42 is a perspective view of the Push Rod of the embodiment of the articulating broach handle of FIG. 35.
Figure 43:
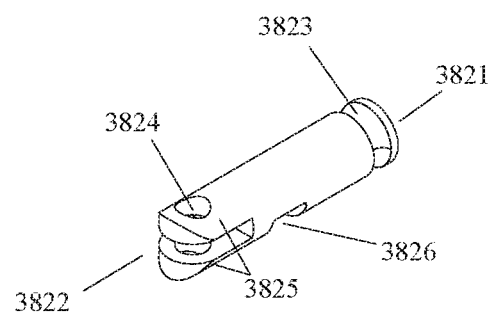
FIG. 43 is a perspective view of the Clasp Rod of the embodiment of the articulating broach handle of FIG. 35.

FIG. 37 depicts the Main Section 3200 having a length consistent with the Main Section of Embodiments 1 and 2. The distal end 3201 consists of a slight bend of 22.5 degrees and a cylindrical attachment 3202 having a cavity 3203 which houses a first end 3811 of the Push Rod 3810 (FIG. 42). The 22.5 degree bend allows the instrument to create a straight tool when rotated accordingly. The Push Rod 3810 is cylindrical in shape and consists of a First End 3811, a Groove 3813, sized to fit a Rod Spinlock Pin 3830, extending the circumference is located near the First End, a second end 3812 and a Slot 3814 perpendicular to the length of the Push Rod 3810 located near the Second End 3812. The Push Rod 3810 is held in place to the Main Section 3200 by Rod Spinlock Pin 3830 which extends through a cylindrical Chanel 3205 near the distal end of the Main Section and is seated in the Groove 3813 of the Push Rod. The distal most aspect of the cylindrical attachment 3202 has a number of flat surfaces 3204 around the circumference. The number of flat surfaces 3204 may vary from four (4) to thirty-two (32), preferably having eight flat surfaces. The number of flat surfaces 3204 determines the amount of incremental rotation. In the example shown in FIG. 37, a distal end having eight (8) flat surfaces allows articulation between the Main Section 3200 and the Center Section 3300 in 45 degree increments, allowing for a full 360 degree rotation between the two sections. It is also contemplated that the distal end has no flat surfaces and thus rotation between the Main Section and the Center Section may be accomplished in no fixed increment amount.

FIGS. 38A and 38B depict the Center Section 3300. Both the distal end 3302 and the proximal end 3301 have a bend with respect to the body 3305 of the Center Section 3300. The amount of bend at the proximal end and distal end are equal and similarly equal to the bend at the distal end 3201 of the Main Section 3200. Both the proximal end 3301 and the distal end 3302 have a Cavity 3306 which houses a Second End 3812 of the Push Rod 3810. The Cavity 3306 has flat surfaces 3304 on its circumference corresponding to the flat surfaces 3204 of the distal end of the Main Section 3200 and proximal end 3702 of the Connecting Body 3700. When the distal end 3202 of the Main Section is seated in the Cavity 3306 of the proximal end Center Section, the two sections are not able to articulate with respect to each other. This is similar as to when the proximal end of the Connecting Body is seated in the Cavity of the distal end 3302 of the Center Section 3300.

Near the proximal end 3301 of the Center Section, perpendicular to the Cavity 3306 is an opening 3307 extending to Cavity 3306. A first Cam Grip 3400A for moving the Center Section distally from the Main Section comprises a Thumb Wheel 3401, a Shaft 3402 which is eccentric to the center of the Thumb Wheel and a Guide 3403 which is similarly eccentric to the center of the Shaft, is inserted into the opening 3307. The diameter of the Opening 3307 corresponds to the diameter of the Shaft 3402 and the Slot 3814 of the Push Rod 3810 is sized to accept the Guide 3403. The Shaft 3402 includes a Retaining Groove 3402-1. The Grip Cam is removably attached to the Center Section by two (2) Wheel Lock Pins 3840 inserted through Pin Openings 3303 and the shaft of the Wheel Lock Pins 3840 fit within the Retaining Groove 3402-1 of the Shaft 3402. Tab 3404 functions as a locking mechanism when the Cam Grip is rotated counterclockwise to secure the Main Section to the Center Section such that the Cam Grip does not move when a surgeon strikes the Force Disc.

The distal end 3302 of the Center Section 3300 is similarly configured as the proximal end 3301 of the Center Section and includes a second Cam Grip 3400B similarly attached to the Center Section 3300.

Connecting Body 3700 interfaces with Center Section 3300 and Broach Section 3500. Connecting Body 3700 has a proximal end 3701 that is configured similar to the distal end of the Main Section in that it consists of a slight bend and a cylindrical attachment 3702 having a cavity 3707 which houses a first end 3811 of a second Push Rod 3810 (FIG. 42). The proximal most aspect of the cylindrical attachment 3702 has a number of flat surfaces 3704 around the circumference. Similar to the distal end of the Main Section the number of flat surfaces 3704 may vary depending on the size of incremental articulation desired. The number of flat surfaces of the Connecting Body and the Main Section do not have to be equal.

The distal end 3706 of the Connecting Body 3700 includes an extended Mating Surface 3705 to releasable connect to the Broach Section 3500. The shape of the Mating Surface 3705 corresponds to a Cavity 3508 at the proximal end 3501 of the Broach Section 3500. The distal end 3706 of the Connecting Body 3700 includes an opening 3708 into which the proximal end 3821 of the Clasp Rod 3820 is seated therein. The Clasp Rod 3820 is a cylindrical shape connecting member and is held in place to the Connecting Body 3700 by a Rod Spinlock Pin 3830 extending a channel (not shown). Similar to the Push Rod 3810, the proximal end 3821 of the Clasp Rod 3820 includes a groove 3823 extending around the Clasp Rod's circumference into which the Rod Spinlock Pin 3830 is seated.

Figure 44:
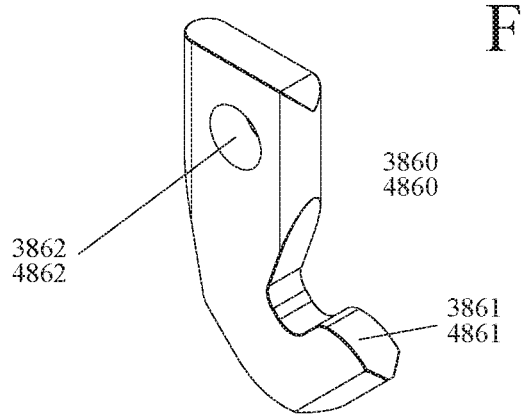
FIG. 44 is a perspective view of the Broachlock of the embodiment of the articulating broach handle of FIG. 35.

The Clasp Rod 3820, as mentioned, allows the Connecting Body 3700 to be connected to the Broach Section 3500. Near the middle of the Clasp Rod 3820 is a slot 3826 that extends to the center of the Clasp Rod. This slot functions similar to the slot 3814 of the Push Rod 3810. The distal end 3822 of the Clasp Rod has two prongs 3825 with each prong have a channel 3824 allowing the Pivot Pin 3850 to be inserted through opening 3862 of the Broachclock 3860 and opening 3505 of the Broach Section to hold the Broachlock (FIG. 44).

The Broach Section 3500 (FIGS. 40A, B) is movably connected to the Connecting Body 3700 via the Clasp Rod 3820. The proximal end 3501 includes a cavity 3508 allowing the distal end 3821 of the Clasp Rod to be seated therein. Near the proximal end 3501 is a channel 3505 on one side of the Broach Section that extends through to the Cavity 3508. Similar to the opening 3302 in the distal and proximal ends 3301, 3302 of the Center Section 3300, the Broach Section 3500 includes a similar opening. This allows a third Grip Cam 3400C to be seated therein and secured to the Broach Section by two Wheel Secure Pins 3840 (FIG. 47).

Figure 46:
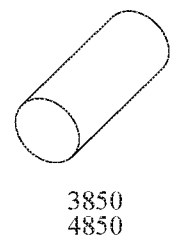
FIG. 46 is a perspective view of the Pivot Pin of the embodiment of the articulating broach handle of FIG. 35.

The Broach Section 3500 houses the Broachlock 3860 (FIG. 44) which releasably connects a Broach to the Broach Handle. The distal end 3502 of the Broach Section includes an opening 3503 sized to accept the proximal end of the Broach 3900. The proximal end of the Broach includes a recessed section allowing the hook 3861 of the Broachlock to engage the Broach and secure the Broach to the Broach Handle. To allow the Broachlock to disengage from the Broach, the distal end 3502 of the Broach Section includes an opening 3507 on the underside allowing the Broachlock 3860 via channel 3862 to pivot about the Pivot Pin 3850 (FIG. 46) secured to the Clasp Rod 3820 in a disengaged state. Engagement and disengagement of the Broachlock to the Broach is controlled by the third Grip Cam 3400C.

To prevent the Broach 3900 from rotating a Broach Lock Pin 3901 is inserted in a cavity (not shown) at the proximal end of the Broach and a corresponding cavity 3504 on the distal end 3502 of the Broach Section.

Method of Use

Using the broach handle of the Third Embodiment, a surgeon in preparing, for example, a medullary canal to have a prosthetic stem component inserted will connect the broach to the broach handle by rotating the Third Grip Cam in a counterclockwise direction, moving the Broach Section in a linear distal direction causing the Broachlock to extend below the underside of the Broach Section. A broach is inserted into the distal end of the Broach Section and the Broach Lock Pin engages the Broach Section, preventing the Broach from rotating. The Broach is secured to the Broach Section by the surgeon rotating the Third Grip Cam in a clockwise direction causing the Broach Section to engage the Connecting Body.

Depending on the physical characteristics of the patient, the surgeon may need to offset the Force Disc of the Broach Handle from the linear axis of the Broach. The surgeon may configure the Broach Handle in at least one of five different configurations, (1) Straight; (2) High Offset Right; (3) High Offset Left; (4) Double Offset Right; and (5) Double Offset Left. (see FIGS. 48A-48E) The surgeon using the First and Second Grip Cams can articulate the Main Section and the Center Section with respect to each other and to the Connection Body, offsetting the Force Disc. This is accomplished by rotating the First Grip Cam or the Second Grip Cam or both in a clockwise direction. If the surgeon rotates the First Grip Cam, the Center Section is moved distally in a linear direction, disengaging from the Main Section. Once disengaged the surgeon can then articulate (rotate) the Main Section to offset the Force Dome. Once there is sufficient offset, the First Grip Cam is rotated in a counterclockwise direction causing the Center Section to move in a proximal direction engaging with the Main Section to prevent further articulation. The Center Section can similarly be articulated with respect to the Connecting Body using the Second Grip Cam. Once there is sufficient offset, the surgeon may position the broach handle with broach such that the broach is inserted into the medullary canal through a surgical incision. The broach handle and broach are positioned allowing the surgeon operate on the medullary canal by exerting a force onto the broach handle by striking the Force Disc. Once the medullary canal is sufficiently prepared, the broach handle and broach are removed from the medullary canal allowing a prosthetic stem component to be installed.

As discussed above in connection with Embodiment 1, a unique feature of the present invention is that the Center Section can articulate with respect to either the Main Section, the Broach Section or both. An advantageous feature of this articulation in combination with the bends of the Main, Center and Broach Sections is that Main Section can be offset spatially from the Broach Section yet maintain parallel along the longitudinal axes (a-a and b-b) FIG. 1. The amount of offset or spatial separation between the Main Section and the Broach Section may be adjusted by the amount of articulation (rotation) between the Main Section and the Center Section and/or the Center Section and the Broach Section. This offset is desirable depending on the physical features of the patient. That is, for a slender patient undergoing hip replacement surgery the surgeon does not require as much offset as for a patient who is more rotund about the midsection and hip area. By maintaining parallel but spatially offset longitudinal axes between the Main Section and the Broach Section, the force delivered by the surgeon onto the Force Disc is transmitted in the same linear direction onto the Broach Section and ultimately the Broach. (see FIGS. 48D and 48E for a double offset, left and right)

Figure 48A:
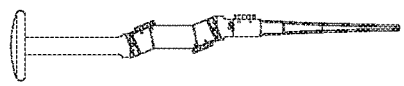
FIGS. 48A-48E are perspective views of different configurations of the embodiment of the articulating broach handle of FIG. 35.
Figure 48B:
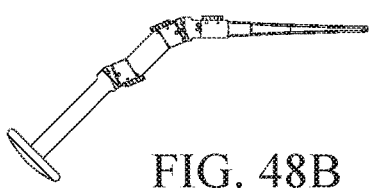
Figure 48C:
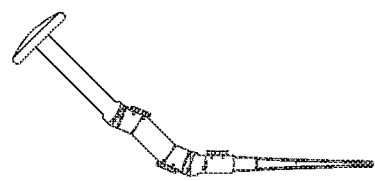
Figure 48D:
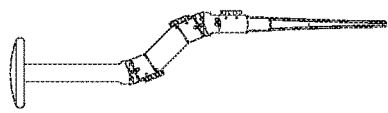
Figure 48E:
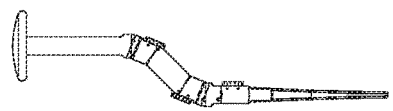

When applicable the Main Section may form approximately a 45 degree angle with the Broach Section when the Broach handle is in a high offset, left or right, as depicted in FIGS. 48B and 48C.

The ability to articulate the various sections of the Broach Handle with respect to one another allows the Broach Handle to be used on either the left or right side and can accommodate differences in the physical characteristics of patients, such as their girth.

Embodiment 4

Figures 49A, 49B:
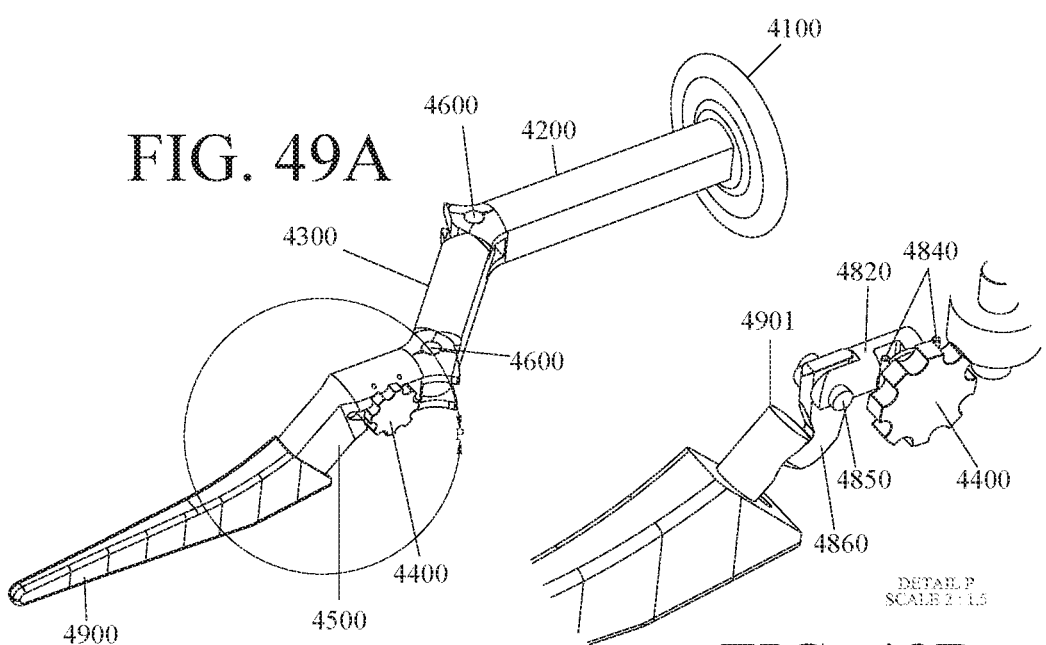
FIG. 49A is a perspective view of another embodiment of an articulating broach handle.
FIG. 49B is a exploded view of a section of the embodiment of the articulating broach handle of FIG. 49A.

FIGS. 49A and 49B depict a fourth embodiment of the present invention as described in the context of an articulating broach handle 4000. The articulating broach handle from the proximal end to the distal end consists of a Force Disc 4100, a Main Section 4200 (FIG. 50), a Center Section 4300 (FIG. 51), and a Broach Section 4500 (FIGS. 52A, 52B). The Main Section and the Center Section may articulate with respect to one another via a pivot dowel 4600. A pivot/articulation means allows articulation of the Center Section 4300 with respect to the Broach Section 4500. A cam mechanism, Grip Cam 4400, a Clasp Rod 4820 (FIG. 53) and two Wheel Secure Pins 4440 allows a Broach 4900 to be releasably engaged with Broach Handle 4000. The Grip Cam 4400 functions similar to Grip Cam 3400C of the Third Embodiment.

The Force Disc 4100 is similar to and provides the same function as the Force Disc of Embodiments 1, 2 and 3. Force Disc 4100 is secured to the proximal end 4202 of the Main Section 4200.

FIG. 50 depicts the Main Section 4200 having a length consistent with the Main Section of Embodiments 1, 2 and 3. The distal end 4201 consists of a two flared extensions 4203 having two angled surfaces 4203 forming a center point. Each surface is angled by 22.5 degrees. The width of the flared distal end is greater than the width of the Main Section body 4205. Each flared extension includes a hole 4204 allowing a Pivot Dowel 4600 to be pressed fit into the holes. The two flared ends are spaced apart to allow the proximal end of the Center Section to be inserted between the flared ends.

Figure 51:
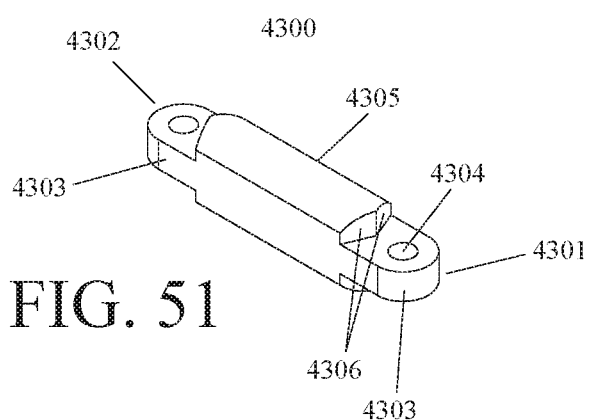
FIG. 51 is a perspective view of the Center Section of the embodiment of the articulating broach handle of FIG. 49A.

FIG. 51 depicts the Center Section 4300 having a length consistent with the Center Section of Embodiments 1, 2 and 3. The cross section of the body 4305 of the Center Section is generally rectangular having a height and width. Both the distal end 4302 and the proximal end 4301 form a spacer 4303 having a semi-circular end and a channel 4304 whose diameter is slightly larger than the diameter of holes 4204 of the Main Section. The height of the spacer 4303 is smaller than the overall height of the Center Section body such it can be inserted between the two flared extensions 4203 of the Main Section, and the proximal end of the body 4305 includes angled surfaces 4306 above and below the spacer member, whereby the angled surfaces 4306 correspond to the angled surfaces 4203 of the Main Section. The proximal end 4301 of the Center Section is connected to the distal end 4201 of the Main Section via the Pivot dowel 4600 extending through holes 4204 and 4304. The Pivot dowel is press fit into holes 4204. Because hole 4304 of the Center Section has a greater diameter than the Pivot dowel, the Center Section can pivot about the Pivot dowel allowing one each of the corresponding angled surfaces of the Main Section and Center Section to mate, forming an angle of 135 degrees. Depending on the direction of pivot of the Center Section with respect to the Main Section, the Broach Handle may be configured as a left side Broach Handle or a right side Broach Handle. The Main Section and the Center Section may also form a straight connection configuration. The distal end 4302 of the Center Section is structured the same as the proximal end 4301 and connects to the proximal end of the Broach Section 4500.

The Broach Section 4500 is structure similar to the Broach Section 3500 of the Third Embodiment, allowing a Broach 3900 to be releasably connected to the Broach Handle 4000. The proximal end 4501 of the Broach Section, however, is different than the proximal end of the Broach Section of Embodiment 3. The Broach Section 4500 may include a bend 4510 of 135 degrees as shown in FIGS. 49A, 52A and 52B.

The Broach Section Section 4500 is movably connected to the Center Section via Pivot dowel 4600 in a manner similar to the connection of the Center Section the Main Section. More precisely, the proximal end 4501 of the Broach Section is structured similarly as the distal end 4201 of the Main Section and allows the articulation of the Center Section 4500 with respect to the Broach Section 4500 forming either a left side or right side Broach Handle with a 135 degree bend formed between the Center Section and the Broach Section. Similar to the Main Section and the Center Section, the Center Section and the Broach Section may form a straight connection configuration.

The proximal end 4501 includes a cavity 4508 allowing the Clasp Rod 4820 to be seated therein. Near the proximal end 4501 is a channel 4505 on one side of the Broach Section that extends through to the Cavity 4508. This is similar to the Broach Section 3300 of Embodiment 4. Channel 4505 allows Grip Cam 4400 to be seated therein and is secured to the Broach Section by two Wheel Secure Pins 4840 (FIG. 49B) which are inserted through two channels perpendicular to the longitudinal axis of the proximal end of the Broach Section.

The Clasp Rod 4820 is a cylindrical shape connecting member and is held in place to the Connecting Body 3700 by a Rod Spinlock Pin 3830 extending a channel (not shown). Similar to the Push Rod 3810, the proximal end 3821 of the Clasp Rod 3820 includes a groove 3823 extending around the Clasp Rod's circumference into which the Rod Spinlock Pin 3830 is seated.

The Clasp Rod 4820 functions to releasably connect the Broach 4900 to the Broach Handle 4000. Near the middle of the Clasp Rod 3820 is a slot 4826 that extends to the center of the Clasp Rod. This slot functions similar to the slot 3814 of the Push Rod 3810 of the Third Embodiment, whereby the Guide 4403 of the Grip Cam 4400 located once the Grip Cam is attached to the Broach Section. The distal end 4822 of the Clasp Rod has two prongs 4825 with each prong have a channel 4824 allowing the Pivot Pin 4850 to be inserted through opening 4862 of the Broachlock 4860 and opening 4505 of the Broach Section to hold the Broachlock.

Grip Cam 4400 (FIG. 41) is structured similar to the Grip Cams 3400A, B, C of Embodiment 3, having a Thumb Wheel 4401, a Shaft 4402 and a Guide 4403, The Shaft 4402 includes a Retaining Groove 4402-1. Tab 4404 functions as a locking mechanism when the Cam Grip is rotated clockwise to secure the Broach Section to the Center Section such that the Cam Grip does not move when a surgeon strikes the Force Disc. Refer to Embodiment 3 for the description of the Grip Cam 4400. Elements of the Grip Cam are the same as those in Embodiment 3 with the exception that the reference designators start with a "4" and not a "3".

The Broach Section 4500 houses the Broachlock 4860 (Similar to the Grip Cam, Embodiment 3 describes the structure of the Broachlock. Refer to FIG. 44 and the accompanying description. Reference designators for Embodiment 4 begin with a "4" while reference designators for Embodiment 3 begin with a "3". The distal end 4502 of the Broach Section includes an opening 4503 sized to accept the proximal end of the Broach 4900. The proximal end 4901 of the Broach 4900 includes a recessed section allowing the hook 4861 of the Broachlock 4860 to engage the Broach and secure the Broach to the Broach Handle (FIG. 49B). To allow the Broachlock to disengage from the Broach, the distal end 4502 of the Broach includes an opening 4509 on the underside allowing the Broachlock 4860 via channel 4862 to pivot about the Pivot Pin 4850 (FIG. 46) secured to the Clasp Rod 4820 (FIG. 53) in a disengaged state. Engagement and disengagement of the Broachlock to the Broach is controlled by Grip Cam 4400.

To prevent the Broach 4900 from rotating a Broach Lock Pin (the same as 3901 of Embodiment 3) is inserted in a cavity (not shown) at the proximal end of the Broach and a corresponding cavity 4504 on the distal end 4502 of the Broach Section.

Method of Use

The Broach Handle of the Fourth Embodiment allows a surgeon to configure the Broach Handle for a right lateral offset broach, left lateral offset broach or as a linear broach. Using the broach handle of the Fourth Embodiment, a surgeon will connect a broach to the broach handle by rotating the Grip Cam in a counterclockwise direction, moving the Clasp Rod 4820 in a linear distal direction causing the Broachlock 4860 to extend below the underside of the Broach Section. A broach is inserted into the distal end 4502 of the Broach Section and a Broach Lock Pin is inserted into cavity 4504 of the Broach Section, preventing the Broach from rotating about its linear axis. The Broach is secured to the Broach Section by the surgeon rotating the Grip Cam in a clockwise direction causing the Clasp Rod 4820 to move in a proximal direction within cavity 4508. The Grip Cam is prevented from further rotation by Tab 4404. The tab is a quick stop providing like a top dead center.

Depending on the physical characteristics of the patient, the surgeon may need to offset the Force Disc of the Broach Handle from the linear axis of the Broach. The surgeon may adjust/swing/articulate the Main Section and the Center Section with respect to each other and to the Broach Section, offsetting the Force Disc for either a right lateral offset or a left lateral offset. This is accomplished by adjusting the various sections with respect to one another such that the angled surfaces are in contact with each other. The relative positions of the sections are maintained until the surgeon applies force to adjust one section (Main, Center, End Connect) with respect to the other section.

The ability to articulate the various sections of the Broach Handle with respect to one another allows the Broach Handle to be used on either the left or right side.

Although the present invention has been described in considerable detail with reference to certain embodiments thereof, other embodiments are possible. Therefore, the spirit and scope of the appended claims should not be limited to the description of the embodiments contained therein. It should be understood that various changes, substitutions, additions and alterations can be made by one skilled in the art without departing from the spirit and scope of the invention as defined by the appended claims. Moreover, the scope of the present application is not intended to be limited to the particular embodiment(s) of the device, process, machine, manufacture and composition of matter, means, methods and or steps described in the specification. As one of ordinary skill in the art will readily appreciate from the disclosure herein, processes, machines, manufacture, composition of matter, means, methods or steps, presently existing or later to be developed that perform substantially the same function or achieve substantially the same result as the corresponding embodiments described herein may be utilized according to the present invention.

What is claimed:

1. An articulating surgical tool handle comprising:
a force disc;
a main section having a first end connected to the force disc;
a center section;
a connector body;
a broach section configured for connection to a tool;
a first cam mechanism connecting, and enabling relative rotation between, a second end of the main section and a first end of the center section around an axis of rotation that extends along longitudinal axes of the second end of the main section and the first end of the center section;
a second cam mechanism connecting, and enabling relative rotation between, a second end of the center section and a first end of the connector body around an axis of rotation that extends along longitudinal axes of the second end of the center section and the first end of the connector body; and
a third cam mechanism connecting, and enabling relative rotation between, a second end of the connector body and a first end of the broach section around an axis of rotation that extends along longitudinal axes of the second end of the connector body and the first end of the broach section,
wherein at least one of the cam mechanisms enables 360 degrees of relative rotation.

2. The articulating surgical tool handle of claim 1, wherein at least one of the relative rotations is in discrete increments.

3. The articulating surgical tool handle of claim 2, wherein each discrete increment is 45 degrees of rotation.

4. The articulating surgical tool handle of claim 1, wherein each relative rotation is a fixed relative rotation.

5. The articulating surgical tool handle of claim 1, wherein the cam mechanisms are configured such that the articulating surgical tool handle has a double offset configuration.

6. The articulating surgical tool handle of claim 5, wherein in the double offset configuration, the main section is laterally offset from the broach section and longitudinal axes of at least portions of the main section and broach section are substantially parallel to each other.

7. The articulating surgical tool handle of claim 6, wherein the offset of the main section and broach section is adjustable.

8. The articulating surgical tool handle of claim 1, wherein the tool is a broach.

9. An articulating surgical tool comprising the articulating surgical tool handle of claim 1 connected to a broach.

10. An articulating surgical tool handle comprising:
a force disc;
a main section having a first end connected to the force disc;
a center section;
a connector body;
a broach section configured for connection to a tool;
a first cam mechanism connecting, and enabling relative rotation between, a second end of the main section and a first end of the center section around an axis of rotation that extends along longitudinal axes of the second end of the main section and the first end of the center section;
a second cam mechanism connecting, and enabling relative rotation between, a second end of the center section and a first end of the connector body around an axis of rotation that extends along longitudinal axes of the second end of the center section and the first end of the connector body;
a third cam mechanism connecting, and enabling relative rotation between, a second end of the connector body and a first end of the broach section around an axis of rotation that extends along longitudinal axes of the second end of the connector body and the first end of the broach section,
wherein at least one of the main section, center section, connector body or broach section has at least one bend in a longitudinal extent thereof.

11. The articulating surgical tool handle of claim 10, wherein at least one of the cam mechanisms enables 360 degrees of relative rotation.

12. The articulating surgical tool handle of claim 10, wherein the at least one bend comprises a bend in the main section at the second end, bends in the center section at the first end and the second end in opposite directions of each other, a bend in the connector body at the second end, and a bend in the broach section at the first end.

13. The articulating surgical tool handle of claim 12, wherein the longitudinal axes of the first and second ends of the center section are generally parallel to each other.

* * * * *